(12) United States Patent  
Singhatat et al.

(10) Patent No.: US 7,338,492 B2
(45) Date of Patent: Mar. 4, 2008

(54) CROSS-PIN GRAFT FIXATION, INSTRUMENTS, AND METHODS

(75) Inventors: Wamis Singhatat, Malvern, PA (US); Steven E. Fitts, Largo, FL (US)

(73) Assignee: Linvatec Corporation, Largo, FL (US)

( * ) Notice: Subject to any disclaimer, the term of this patent is extended or adjusted under 35 U.S.C. 154(b) by 384 days.

(21) Appl. No.: 10/693,464

(22) Filed: Oct. 24, 2003

(65) Prior Publication Data

US 2004/0087953 A1    May 6, 2004

Related U.S. Application Data

(63) Continuation-in-part of application No. 10/658,052, filed on Sep. 9, 2003, which is a continuation-in-part of application No. 10/438,510, filed on May 15, 2003.

(60) Provisional application No. 60/380,376, filed on May 15, 2002, provisional application No. 60/423,022, filed on Nov. 1, 2002.

(51) Int. Cl.
*A61F 2/30* (2006.01)
(52) U.S. Cl. .................. 606/72; 606/98; 623/13.12
(58) Field of Classification Search ............ 606/72–73, 606/232; 623/13.11–13.14; 128/898
See application file for complete search history.

(56) References Cited

U.S. PATENT DOCUMENTS

| | | | |
|---|---|---|---|
| 3,973,277 A | 8/1976 | Semple et al. |
| 4,834,752 A | 5/1989 | Van Kampen |
| 4,901,711 A | 2/1990 | Goble et al. |
| 4,985,032 A | 1/1991 | Goble |
| 5,004,474 A | 4/1991 | Fronk et al. |
| 5,067,962 A | 11/1991 | Campbell et al. |
| 5,152,764 A | 10/1992 | Goble |
| 5,192,321 A | 3/1993 | Strokon |
| 5,234,434 A | 8/1993 | Goble et al. |
| 5,266,075 A | 11/1993 | Clark et al. |
| 5,300,077 A | 4/1994 | Howell |
| 5,314,429 A | 5/1994 | Goble |
| 5,350,380 A | 9/1994 | Goble et al. |
| 5,354,300 A | 10/1994 | Goble et al. |
| 5,356,435 A | 10/1994 | Thein |
| 5,376,119 A | 12/1994 | Zimmermann et al. |
| 5,393,302 A | 2/1995 | Clark et al. |
| 5,397,356 A | 3/1995 | Goble et al. |
| 5,431,651 A | 7/1995 | Goble |
| 5,562,671 A | 10/1996 | Goble et al. |
| 5,601,562 A | 2/1997 | Wolf et al. |
| 5,674,224 A | 10/1997 | Howell et al. |
| 5,688,284 A | 11/1997 | Chervitz et al. |

(Continued)

OTHER PUBLICATIONS

Brochure Entitled Cross-Screw System, Stryker Endoscopy 1000-900-373 Rev. B.

(Continued)

*Primary Examiner*—Eduardo C. Robert
*Assistant Examiner*—Mary Hoffman

(57) ABSTRACT

A two piece graft fixation arrangement includes a graft block engageable with a graft and a transverse member engageable with the graft block to fix the graft block in a bone tunnel. Instruments and methods are presented for installing a graft in a bone tunnel and anchoring the graft with a transverse member placed through a transverse bore intersecting the bone tunnel.

1 Claim, 16 Drawing Sheets

U.S. PATENT DOCUMENTS

| | | | |
|---|---|---|---|
| 5,704,936 A * | 1/1998 | Mazel | 606/61 |
| 5,849,013 A | 12/1998 | Whittaker et al. | |
| 5,891,150 A | 4/1999 | Chan | |
| 5,895,425 A | 4/1999 | Grafton et al. | |
| 5,918,604 A | 7/1999 | Whelan | |
| 6,066,173 A | 5/2000 | McKernan et al. | |
| 6,113,604 A | 9/2000 | Whittaker et al. | |
| 6,132,433 A | 10/2000 | Whelan | |
| 6,306,138 B1 | 10/2001 | Clark et al. | |
| 6,325,804 B1 | 12/2001 | Wenstrom, Jr. et al. | |
| 6,371,124 B1 | 4/2002 | Whelan | |
| 6,379,384 B1 | 4/2002 | McKernan et al. | |
| 6,387,129 B2 | 5/2002 | Rieser et al. | |
| 6,499,486 B1 | 12/2002 | Chervitz et al. | |
| 6,517,546 B2 | 2/2003 | Whittaker et al. | |
| 6,537,319 B2 | 3/2003 | Whelan | |
| 6,540,783 B1 | 4/2003 | Whittaker et al. | |
| 6,712,849 B2 * | 3/2004 | Re et al. | 623/13.14 |
| 6,923,824 B2 * | 8/2005 | Morgan et al. | 606/232 |
| 2001/0044627 A1 | 11/2001 | Justin | |
| 2001/0053934 A1 | 12/2001 | Schmieding | |
| 2002/0019635 A1 | 2/2002 | Wenstrom, Jr. et al. | |
| 2002/0058941 A1 | 5/2002 | Clark et al. | |
| 2002/0087160 A1 | 7/2002 | Clark et al. | |
| 2002/0108622 A1 | 8/2002 | Whelan | |
| 2002/0133165 A1 | 9/2002 | Whittaker et al. | |
| 2002/0156484 A1 | 10/2002 | McKernan et al. | |
| 2002/0173849 A1 | 11/2002 | McKernan et al. | |
| 2003/0009217 A1 | 1/2003 | McKernan et al. | |
| 2003/0050642 A1 | 3/2003 | Schmieding | |
| 2003/0065391 A1 | 4/2003 | Re et al. | |
| 2003/0120343 A1 | 6/2003 | Whelan | |
| 2003/0130666 A1 | 7/2003 | Whittaker et al. | |

OTHER PUBLICATIONS

Brochure Entitled Sometimes Revolutions Cannot Be Seen ACL Cross-Pin System Surgical Technique—Arthrotek 2002.

* cited by examiner

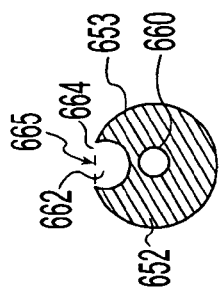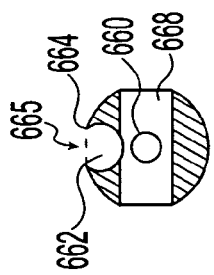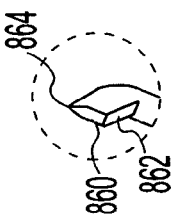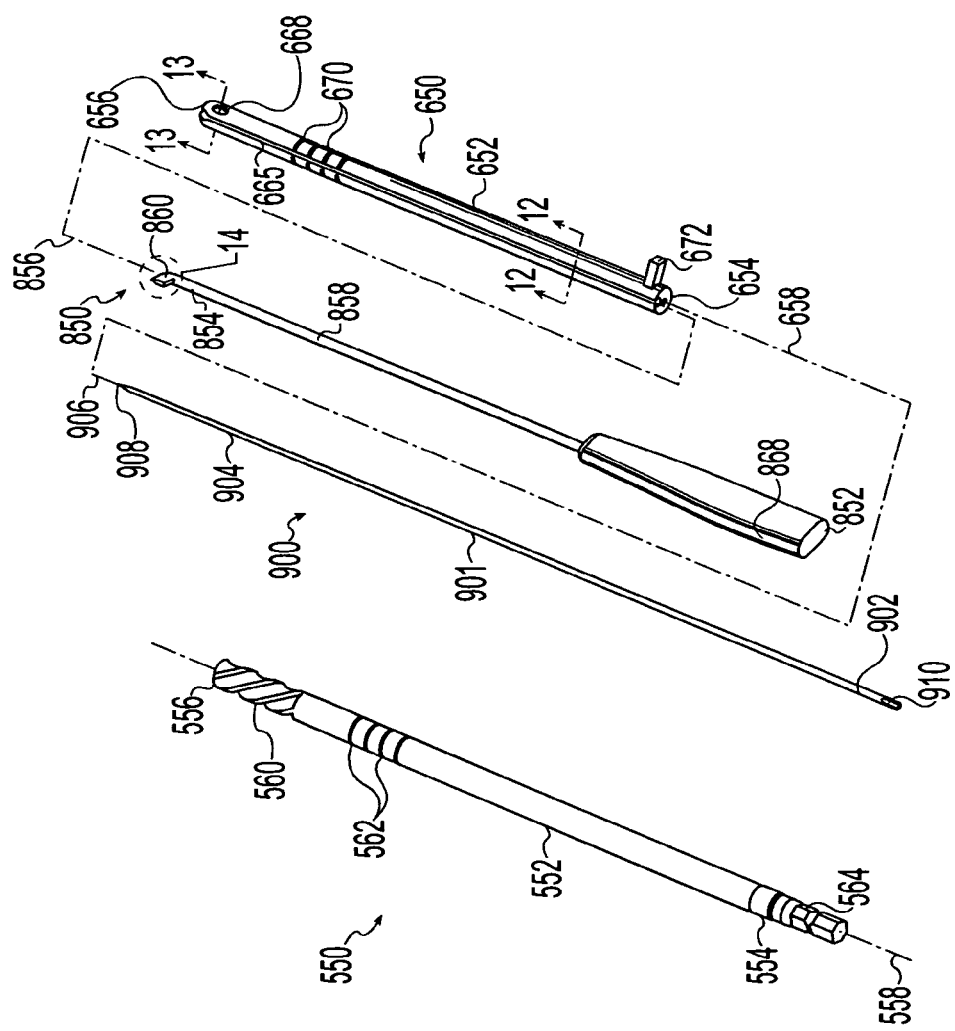

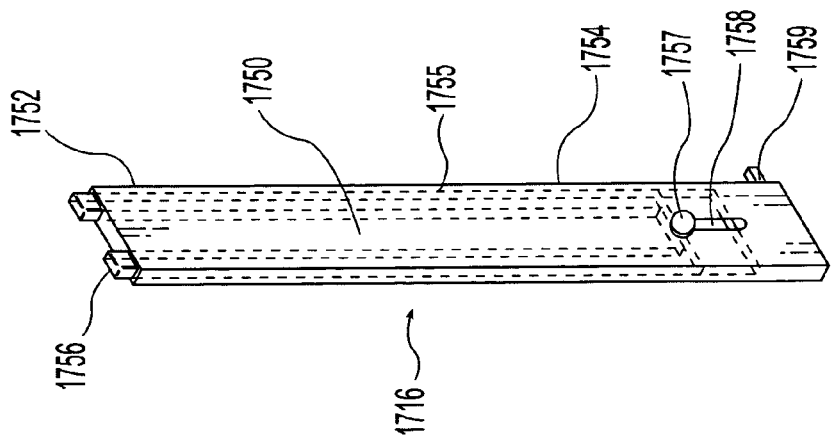
Fig. 30
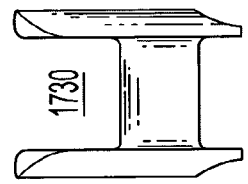
Fig. 29
Fig. 28
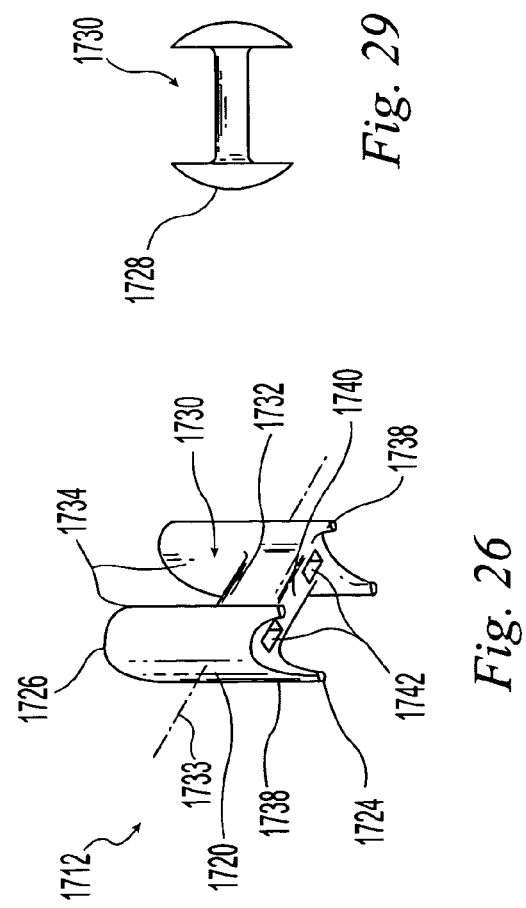
Fig. 26
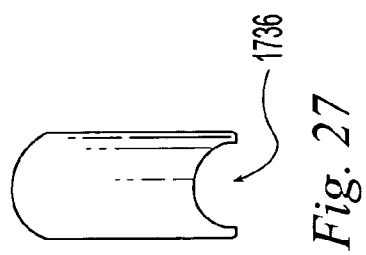
Fig. 27

CROSS-PIN GRAFT FIXATION, INSTRUMENTS, AND METHODS

CROSS-REFERENCE TO RELATED APPLICATIONS

This application is a continuation-in-part of U.S. patent application Ser. No. 10/658,052, filed Sep. 9, 2003, which is a continuation-in-part of U.S. patent application Ser. No. 10/438,510, filed May 15, 2003 which claims the benefit of U.S. Provisional Application No. 60/380,376 filed May 15, 2002, and U.S. Provisional Application No. 60/423,022 filed Nov. 1, 2002.

FIELD OF THE INVENTION

The invention relates to soft tissue repair and reconstruction. More particularly, the invention relates to the fixation of a graft within a bone tunnel. Still more particularly, the invention relates to improvements in the use of a transverse pin to retain a graft within a bone tunnel.

DESCRIPTION OF THE PRIOR ART

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing within these bone tunnels a graft ligament. In many applications, such as in the knee joint, such procedures may be performed arthroscopically. The graft ligament may be an autograft, an allograft, a xenograft, and/or it may be totally artificial and synthetic. The most common types of graft ligaments include ones which may be bone-tendon-bone or soft tissue (such as semitendinosus and gracilis tendons), both types harvested by techniques well known to those skilled in the art.

The graft ligaments are secured within the bone tunnels in a variety of ways. Of prime importance is the degree to which they can withstand pullout forces prior to complete healing. For example, it is known to use interference screws inserted parallel to the tunnel axis to compress the ends of the graft ligament against the walls of the bone tunnel to secure the graft ligament and promote tissue in-growth.

Recently, cross-pin fixation devices have been developed to retain the graft ligament within the bone tunnel by securing it with a pin extending transversely through the tunnel and the ligament. Cross-pin fixation, although a more complex procedure, generally provides the highest pullout forces.

Various methods are known to achieve cross-pin fixation. All methods require the initial formation of the ligament bone tunnel in the tibia and femur in a conventional manner. All methods also end up with a pin situated transversely through the graft ligament. (As used herein, (1) in the case of a bone-tendon-bone graft, "through" means actually through the bone at one end of the graft and (2) in the case of a soft tissue graft, "through" means the graft ligament is folded over on itself and the pin extends between the folded ligament strands.) The differences between the various cross-pin fixation methods lies primarily in the manner in which the graft ligament is engaged with the cross-pin. One method utilizes bone-tendon-bone grafts and involves pushing or pulling one of the bone ends of the graft into the femoral tunnel and drilling a transverse hole in the femur to place a cannulated pin directly and transversely through the bone end. U.S. Patents representative of this method include the following: U.S. Pat. No. 5,004,474 (Frank et al.); U.S. Pat. Nos. 5,350,380, 5,354,300, 5,397,356, 5,431,651 (FIG. 7, 7A), U.S. Pat. No. 5,562,671 (all to Goble et al.); U.S. Pat. No. 5,688,284 (Chervitz et al.); U.S. Pat. No. 6,066,173 (McKernan et al.) and U.S. Pat. No. 6,113,604 (Whittaker et al.).

This method may be further understood by reference to aforementioned U.S. Pat. No. 5,350,380 (Goble et al.) which shows a bone drill for drilling a ligament bone tunnel from the proximal tibial surface into the femur. The bone drill is used in conjunction with a C-shaped drill guide to position the location of a transverse hole to be drilled through the lateral femoral surface in order to intersect the ligament bone tunnel at a predetermined location. The graft is pulled into the ligament bone tunnel by sutures extending through the tunnel and a tapered transverse pin is screwed into place to secure the graft.

Another method utilizes soft tissue grafts and involves folding the strands of graft material to create a bundle and pushing the bundle into the femoral tunnel. A cannulated guide pin is placed through the graft ligament strands (i.e. at the fold). U.S. Patents representative of this method are U.S. Pat. No. 5,601,562 (Wolf et al.) and U.S. Pat. No. 6,306,138 (Clark et al.)

This method may be further understood by reference to aforementioned U.S. Pat. No. 5,601,562 (Wolf et al.) which discloses a way of pushing a soft tissue graft ligament into a bone tunnel using a notched ligament inserter. A guide wire is then drilled transversely through one of the pair of notches on the inserter to enable a guide pin to be situated within the loop formed by the soft tissue graft. A cannulated cylindrical cross-pin implant is placed over the guide pin and advanced through the transverse tunnel and into the femur on the opposite side of the tunnel to complete the fixation.

Another method also utilizes soft tissue grafts but requires attaching a suture to one end of the graft, placing a loop of the suture in the bone tunnel at the site wherein the transverse pin will be placed, advancing a transverse guide wire or pin through the loop of suture and then pulling or threading the graft over the pin or guide wire (if the latter, then advancing a cannulated pin over the guide wire) to form a fold in the graft ligament. U.S. Patents representative of this method are: U.S. Pat. Nos. 5,266,075 and 5,393,302 (both to Clark et al.); U.S. Pat. No. 5,431,651 (FIG. 7B, 7C to Goble); and U.S. Pat. No. 5,674,224 (Howell et al.).

The method may be further understood by reference to aforementioned U.S. Pat. No. 5,393,302 (Clark et al.) which discloses a method of inserting a soft tissue graft ligament by pushing it into the bone tunnel on a tendon threader having orthogonally oriented slots at its distal end. One pair of opposed slots engages the graft ligament (or suture secured to the graft ligament) in order to position it at the end of the ligament bone tunnel. A transverse pin may then be drilled directly through the other set of opposed slots. The graft ligament can then be looped over the transverse pin.

Another method also utilizes soft tissue grafts but requires a transverse tunnel entirely through the femur at a point intersecting the ligament bone tunnel. A flexible guide wire is placed in the transverse tunnel and its middle portion is pulled out of the ligament bone tunnel entrance forming a guide wire loop. The soft tissue graft ligament is passed through the guide wire loop and folded back on itself. By pulling in opposite directions on the ends of the flexible guide wire, the graft is pulled into place. The guide wire is then used to guide a cannulated cross-pin into place under the graft ligament fold. U.S. Patents representative of this method are U.S. Pat. No. 5,895,425 (Grafton et al.) and U.S. Pat. Nos. 5,918,604 and 6,132,433 (both to Whelan). This method may be further understood by reference to aforementioned U.S. Pat. No. 5,895,425 (Grafton et al.) which shows that, after the formation of the ligament bone tunnel, a transverse bone tunnel is formed entirely through the femur intersecting the end of the ligament bone tunnel at which the graft is to be placed. A flexible guide wire is threaded through this transverse bone tunnel. The central portion of this flexible guide wire is pulled out of the ligament bone tunnel until it is completely outside the body. A soft tissue ligament graft is looped around this flexible guide wire. The ends of the flexible guide wire are then pulled away from each other to draw the flexible guide wire and the looped graft ligament into the ligament bone tunnel. A cannulated transverse pin is then drilled into place across the ligament bone tunnel and the flexible guide wire is withdrawn.

It is also known that the transverse pin need not be exactly perpendicular to the ligament bone tunnel. U.S. Pat. No. 5,688,284 (Chervitz et al.) shows, for example, a variable angle drill guide which enables the transverse pin to be oriented at a desired angle relative to the ligament bone tunnel.

U.S. Pat. No. 6,066,173 (McKeman et al.) shows another method of cross-pinning fixation utilizing a plurality of transverse pins inserted through the ligament within the ligament bone tunnel.

All known cross-pin fixation systems have some disadvantages and it is an object of this invention to overcome these disadvantages. In the case of the first three methods it is difficult and time consuming to place the transverse pin and thread the graft ligament over the cross-pin or guide pin. In the case of the last method, pulling in opposite directions to move a graft perpendicular to the pulling directions is difficult and the flexible guide wire can be kinked or severed by the cross-pin. In the methods involving pushing the graft ligament into place, the diameter of the ligament bone tunnel must be larger than desired in order to accommodate the dimensions of the pusher and the graft ligament such that when the pusher is removed, the bone tunnel is over-sized relative to the graft.

SUMMARY

The present invention provides a graft retaining system for retaining a graft in a bone tunnel.

In one aspect of the invention the graft retaining system includes a graft block having a proximal end and a distal end. The graft block includes a support surface adjacent the distal end for supporting an intermediate connector. At least one connector hole is formed through the support surface. An intermediate connector connects the graft and graft block. The intermediate connector is a suture-like material which forms a loop supported by the support surface of the graft block and at least one end of the loop is threaded through the connector hole and secured to retain it in the connector hole. The system also includes means for attaching the graft block adjacent the bone tunnel at a predetermined point along the length of the tunnel.

In another aspect of the invention the graft retaining system includes a graft block having a proximal end and a distal end. The graft block includes a graft support surface adjacent the distal end for supporting the graft. The system also includes tunnel attachment means for attaching the graft block adjacent the bone tunnel at a predetermined point along the length of the tunnel. The tunnel attachment means is located proximally of the graft support surface such that tensile forces on the graft result in compressive forces on the graft block between the graft support surface and the tunnel attachment means.

In another aspect of the invention the graft retaining system includes a saddle-shaped graft block having a proximal end and a convex distal end bounded by a pair of distally projecting side walls. A cross pin for attaching the graft block adjacent the bone tunnel at a predetermined point along the length of the tunnel is able to be inserted across the bone tunnel transverse to the axis of the bone tunnel to abut the proximal end of the graft block to retain the graft block in the tunnel.

In another aspect of the invention a method for securing a graft in a bone tunnel includes the steps of: providing a graft block having a saddle shaped body having a distal end over which the graft is placed and a proximal end opposite the distal end; placing the graft over the distal end of the graft block with the graft extending proximally past the proximal end of the graft block; providing a transverse member for abutting the proximal end of the graft block; fitting the graft block and graft into the bone tunnel; and inserting the transverse member across the bone tunnel to abut the proximal end of the graft block and fix the location of the graft block within the bone tunnel.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 9 is a perspective view of a tunnel drill bit according to the present invention.

FIGS. 10 and 11 are exploded perspective views of an illustrative set of surgical instruments according to the present invention.

FIG. 12 is a cross sectional view taken along line 12-12 of FIG. 10.

FIG. 13 is a cross sectional view taken along line 13-13 of FIG. 10.

FIG. 14 is a detail view take from FIG. 10.

FIG. 26 is a perspective view of the graft block of FIG. 25.

FIG. 27 is a side plan view of the graft block of FIG. 25.

FIG. 28 is a front plan view of the graft block of FIG. 25.

FIG. 29 is a top plan view of the graft block of FIG. 25.

FIG. 30 is a perspective view of a pushing member for use with the graft block of FIG. 25.

DETAILED DESCRIPTION

Figures 1, 2:
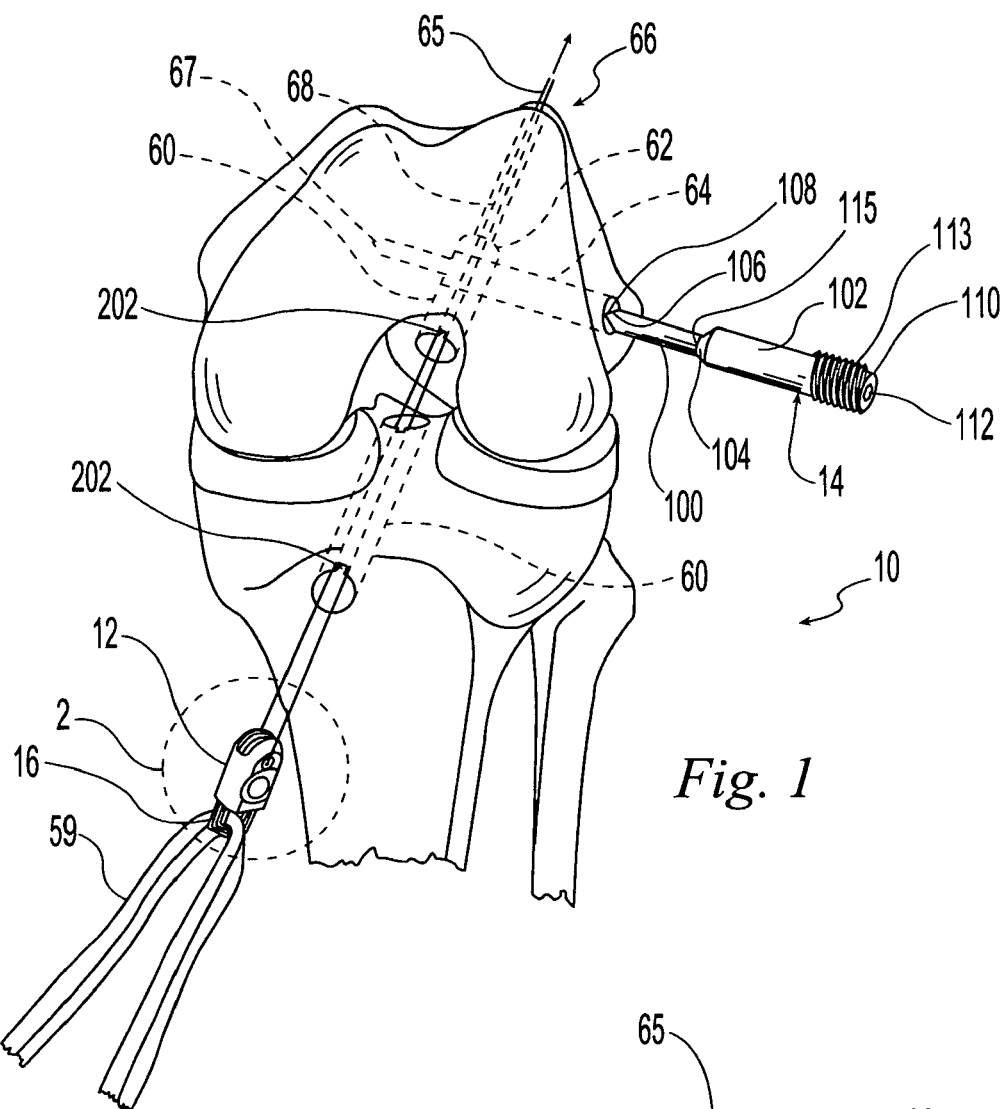
FIG. 1 is a perspective view of a human knee joint showing the insertion of a graft block and cross-pin according to the present invention.
FIG. 2 is a detail view taken from FIG. 1.

Embodiments of a two piece cross-pin graft system include a graft block sized to fit within a bone tunnel and fixation means for fixing the graft block within the bone tunnel. The graft fixation system may be used to attach any appropriate graft including for example supplemental and/or replacement grafts for the soft tissues associated with the skeletal system. For example, the system may be used to replace soft tissues associated with skeletal joints such as the hip, knee, shoulder, wrist, elbow, ankle, vertebral, phalangeal, temporomandibular, and other joints and locations within a body. For example, the graft fixation system may be used to attach, within a bone tunnel, grafts associated with human knee joint tissues such as the anterior cruciate ligament, the posterior cruciate ligament, the medial collateral ligament, and the lateral collateral ligament.

The graft block may be a unitary or multi-piece construction comprising any suitable biocompatible materials. Exemplary materials include metals, polymers, and/or other suitable materials and combinations thereof. For example, the graft block may comprise metals including stainless steels, titanium, titanium alloys, cobalt-chromium steels, nickel-titanium alloys, and/or others. The graft block may comprise nonresorbable polymers including polyolefins, polyesters, polyimides, polyamides, polyacrylates, ploy(ketones), fluropolymers, siloxane based polymers, and/or others. The graft block may comprise resorbable polymers including polyesters (e.g. lactide and glycolide), polyanhydrides, ploy(aminoacid) polymers (e.g. tyrosine based polymers), and/or others. The graft block may comprise other materials including nonresorbable and resorbable ceramics (e.g. hydroxyapitite, calcium sulfate) or biocompatible glasses.

The graft block includes means for attaching the graft to the block. The means for attaching the graft may include an aperture or channel formed in the graft block for receiving a portion of the graft or an additional intermediate connector. The aperture or channel may include a shielded portion with material overlying the aperture or channel to more fully retain and protect the graft and/or intermediate connector from abrasion with the bone tunnel wall. An intermediate connector can, for example, connect to a portion of the graft block and to a portion of the graft by being looped around or through the graft block or by having the graft block molded to the intermediate connector.

The graft and/or intermediate connector may connect to the graft block distally of the fixation means for fixing the graft block within the bone tunnel such that tensile forces on the graft result in compressive forces on the portion of the graft block between the graft and/or intermediate connector and the fixation means. This arrangement eliminates tensile forces on the graft block and prevents tensile breakage of the graft block from being a weak link in the system. In particular, this is helpful where the graft block is made of materials that perform better in compression rather than in tension; e.g. certain ceramics and degradable lactide and/or glycolide based polymers. The present investigators have found that in particular, polylactic acid is stronger, and its strength degrades in a more favorable manner, in vivo when loaded in compression rather than in tension. The intermediate connector may form a loop around a portion of the graft block, for example by being looped through the aperture or channel at the distal end of the graft block and extending beyond the proximal end of the graft block to receive the graft.

The intermediate connector may be flexible to allow it to compress and conform to the graft, graft block, and tunnel so that it can accommodate the smallest possible close fitting tunnel. Likewise, a flexible intermediate connector will distribute the stresses on the graft and graft block for a strong connection. A flexible intermediate connector may be in the form of a flexible member interposed between the graft block and the graft by being, for example, looped through an aperture or channel, having the graft block molded around the intermediate connector, or otherwise. For example, a flexible material may be looped through an aperture and extend beyond the graft block to form a flexible loop for receiving the graft. The intermediate connector may be both flexible and arranged to impart compressive forces on the graft block as described above. A flexible intermediate connector may comprise one or more continuous or closed loops of flexible material or it may comprise a strand of flexible material looped multiple times through or around a portion of the graft block. It may be formed by tying, bonding, otherwise joining, or forming as a single piece. The flexible material may comprise a single piece or a plurality of pieces, such as filaments, that are parallel, twisted, braided, woven, knitted, bonded or otherwise assembled into a cord, tape, fabric, or film. All such forms may herein be sometimes referred to as suture-like materials.

The intermediate connector may comprise metals, resorbable polymers, non-resorbable polymers, and/or other biocompatible materials. For example, the intermediate connector may comprise non-resorbable materials such as stainless steel, titanium, titanium alloys, cobalt-chrome alloys, polyethylene, polyester, polylactic acid, polytetrafluroethylene, and/or silicone polymers. For example, the intermediate connector may comprise high strength polyethylene fiber. The intermediate connector may also comprise resorbable materials such as polylactic acid, polyglycolic acid, caprolactone, and/or polyamino acid polymers.

The graft block may also include means for passing the graft block longitudinally along the bone tunnel. The means for passing may include means for pushing and or pulling the graft block along the bone tunnel. For example, the graft block may be pushed with a rigid shaft engageable with the graft block. The graft block may be pulled with a rigid or flexible member engageable with the graft block. For example the graft block may include an aperture receiving a passing suture that is pulled from the opposite end of the bone tunnel. The graft block may also include means for aligning the graft block in a predetermined orientation within the bone tunnel, for example, in order to align with a transverse aperture to receive a transverse member to fix the graft block at a desired longitudinal position in the bone tunnel. One example of a means for aligning the graft block includes a keyway formed in the graft block for engaging a rotationally rigid member in a known rotational relationship such as a rigid shaft shaped to fit a slot to maintain the graft block in known rotational alignment with the shaft. Another exemplary means for aligning the graft block includes a projection extending radially from the graft block to engage a corresponding slot previously formed in the wall of the bone tunnel at a known circumferential position.

The means for fixing the graft block within the bone tunnel may include an aperture through the graft block or a surface formed on the graft block and a transverse member engageable with the aperture or surface and the wall of the bone tunnel. For example, the graft block may contain a transverse aperture for receiving a transverse pin extending through the aperture and into the bone on either side of the graft block. Alternatively, the graft block may contain a surface for abutting the transverse pin. The transverse member may be any suitable member for fixing the graft block including a pin, screw, bolt, staple and or other suitable member. It may be smooth or it may have means to help retain it in its position such as ribs, teeth, barbs, threads, and/or an expanding anchor arrangement or other suitable means. It may be inserted by pressing, impacting, rotating, or by other suitable means. For example, the transverse member can be a pin having a smooth first end and a second threaded end; the smooth end being received in the aperture of the graft block and the threads engaging the bone adjacent the bone tunnel. Furthermore, the transverse member may be a unitary construction or a multiple piece construction. For example, the transverse member may comprise a multiple piece cross-pin having a distal portion, a proximal cylindrical portion aligned longitudinally with the distal portion, and a junction between the distal and proximal portions. The junction may be any suitable junction to permit rotation of the proximal portion relative to the distal portion such that the proximal portion can be turned to move the distal portion axially without turning the distal portion. For example, the proximal portion can be threaded and the distal portion can be smooth. Such a cross-pin can be used with a graft block or with a graft alone. One advantage of such a two piece cross-pin is that the lack of rotation of the distal end reduces the likelihood of the distal end being entangled in the graft and/or suture. Another advantage of such a two-piece cross-pin is that the distal end can be made non-cylindrical to fit a non-cylindrical graft block aperture such as may be desirable with small bone tunnels where the graft block size is limited and would admit only a small cylindrical cross-pin. By making the pin non-cylindrical, the pin strength can be increased without the need to increase the graft block aperture diameter.

The graft retaining system is installed using a set of instruments for forming a graft bone tunnel and a transverse bone hole intersecting the bone tunnel. For example, the instruments may be used to form aligned tibial and femoral bone tunnels and a transverse bone hole intersecting at least the femoral bone tunnel. As an alternate example, the femoral tunnel may be drilled arthroscopically through a medial portal in the knee joint. The bone tunnel may be formed with a bone tunnel drill bit including depth markings for indicating the depth of the bone tunnel. The bone tunnel drill bit may be provided in an assortment of diameters so that the bone tunnel may be matched to the graft diameter.

The instruments may further include a transverse drill guide for guiding a transverse drill bit to form the transverse hole intersecting the bone tunnel. The drill guide may include a body for mounting modular removable guide rods and drill sleeves perpendicular to one another. The guide rods may be provided in an assortment of diameters to match the tunnel drill bit diameters. Each guide rod may include depth markings to measure the insertion depth of the guide rod into the bone tunnel. The measured insertion depth may then be compared to the tunnel depth measured with the tunnel drill bit to verify that the guide rod is fully seated. The guide rod may further include a transverse throughbore to receive a transverse drill bit to permit the rod to remain fully seated in the bone tunnel while the transverse bone hole is drilled across the tunnel. The transverse throughbore may simulate the position of a transverse aperture in the graft block. Furthermore, the transverse through-bore may act as a depth stop to control the depth of the transverse bone hole. The guide rod may include a first longitudinal cannula for guiding a suture passing pin into the bone beyond the bone tunnel. The guide rod may further include a second longitudinal cannula opening radially outwardly to receive a notch cutter for cutting a rotational reference notch. The rotational reference notch may be referenced by a graft block having a radial projection to position the graft block in a predetermined radial alignment relative to the guide rod. For example, the second longitudinal cannula may be positioned so that it opens radially outwardly in a direction perpendicular to the longitudinal axis of the drill sleeve. A graft block may have a radial projection oriented perpendicular to an axis of a transverse aperture through the graft block. Thus, the graft block will be positioned with the aperture aligned with the drill sleeve when the radial projection is engaged with the rotational reference notch. The guide rods may include additional cannulae for receiving the notch cutter at different circumferential positions. For example, two such cannulae may be provided opposite one another so that rotational reference notches may be formed facing the same direction on both right and left portions of the patients body.

The drill sleeve may have an end that is shaped to engage the bone at a desired entry point for the transverse bone hole. The drill sleeve may include a window for viewing instruments and implants passed through the sleeve. A depth mark may be inscribed on the drill sleeve adjacent the window for determining the depth of implants and instruments in the sleeve.

The transverse drill bit fits closely within the drill sleeve so that the transverse drill bit is guided toward the guide rod positioned within the bone tunnel. The transverse drill bit may be stepped from a smaller diameter to a larger diameter to correspond to a stepped configuration of the transverse member. Furthermore, the transition from the smaller to the larger diameter may provide a shoulder engageable with the guide rod to stop the transverse drill bit from further insertion. The transverse drill bit may include depth markings that can be read adjacent a portion of the drill sleeve to indicate the distance from the shoulder to the end of the drill sleeve adjacent the desired entry point for the transverse bone hole. This measurement may be used to select a transverse member having a length that best fills the distance from the graft block to the desired entry point for the transverse bone hole.

A locator rod may be provided to help hold the drill sleeve in position on the bone and/or to maintain the location of the transverse bone hole when the other instruments are removed from the bone. The locator rod may include an end that is configured to press fit and/or thread into the transverse bone hole. The locator rod may include depth markings that can be read adjacent a portion of the drill sleeve to indicate that the locator rod is engaged with the bone beyond the distal end of the drill sleeve by a predetermined amount. The locator rod may be cannulated to receive an arthroscope for verifying the alignment of the graft block with the transverse bone hole.

A driver for driving the transverse member may include depth markings that can be read adjacent a portion of the drill sleeve to indicate that the transverse member has been driven to a desired depth.

The method of using the instruments may include using an arthroscope directed through the drill sleeve to verify the alignment of the graft block with the transverse bone hole.

FIGS. 1 and 2 illustrate an exemplary graft fixation system in use to replace the anterior cruciate ligament of a human knee. The fixation system 10 comprises a graft block 12, a cross-pin 14 and an intermediate connector in the form of a retaining loop 16. The graft block 12 comprises a body 20 having a proximal end 24 and a distal end 26. The terms "proximal" and "distal" are intended to refer to the orientation of the graft block 12 and the cross-pin 14 within their respective bone tunnels, the proximal end being closer to the tunnel entrance and the distal end being farther away. The body 20 is a generally rectilinear member having a pair of opposed and parallel planar faces 28 and 30 and a pair of opposed and parallel side faces 32 and 34. The planar side faces 28 and 30 may be used to provide relief areas for passing a suture 65 in the bone tunnel 60. When used in this way, the side faces 28 and 30 need not extend the full length of the body 20 as shown, but may alternatively extend only from the distal end to the smaller aperture 42. Alternatively, instead of opposed planar surfaces, relief for the suture 65 may be provided by a groove or trough extending distally from the smaller aperture 42 on each side of the graft block 12. A large aperture 40 extends transversely through the body 20 between faces 28 and 30. A chamfer 41 extends radially outwardly from the large aperture 40 and provides a tapering transition from the faces 28 and 30 to the large aperture 40. A smaller aperture 42 extends parallel to aperture 40 distally thereof. The body 20 is also provided with a pair of parallel longitudinal channels 50 (one side being shown in hidden line in FIG. 2) extending between the proximal 24 and distal 26 ends to receive a portion of the retaining loop 16 and retain it on the graft block 12. The channels 50 are also covered by the sides 32 and 34 to further retain the loop 16 and protect it from abrasion from the bone tunnel. The loop 16, which may be made of a flexible material, has a distal end 56 lying along distal end 26 of the graft block 12 and a proximal end 58 extending below the proximal end 24 of the body 20 to receive a graft 59 to attach it to the graft block 12. In the illustrative embodiment, the loop16 comprises multiple strands of a flexible material. Alternatively, the channels 50 may be made large enough to receive the graft 59 directly. In the illustrative embodiment, the loop16 passes distally over the large aperture 40 and connects the graft 59 proximally of the large aperture such that the portion of the graft block 12 between the loop 16 and the large aperture 40 is placed in compression when the graft 59 is placed in tension.

The side surfaces 32 and 34 may be cylindrical in part. The illustrative graft block 12 may be constructed by milling opposing flat faces 28, 30 on a cylindrical body, molding, sintering, or forming by other suitable methods. The diameter of the graft block body 20 is preferably slightly less than the diameter of the bone tunnel 60 to enable the body 20 to rotate about its axis to facilitate engagement with a cross-pin 14 while maintaining its longitudinal orientation within the tunnel.

The transverse member of this illustrative embodiment comprises a cross-pin 14 having a distal cylindrical section 100, a proximal cylindrical section 102, a tapered transition section 104 between the two cylindrical sections, and a tapered distal end 106 terminating in a pointed distal tip 108. The proximal end 110 of pin 14 is provided with a torque transmitting driver engagement portion such as a recessed, hexagonal drive recess 112. The proximal cylindrical section 102 may be provided with a retention means as previously mentioned. The illustrative embodiment of FIG. 1 includes cancellous screw threads 113 to enable the pin 14 to be advanced into or withdrawn from the femur along its longitudinal axis as it is rotated and to hold its position once it is placed. Alternatively, the cross-pin 14 may have a junction 115 between the proximal 102 and distal 100 sections to permit rotation of the proximal section 102 relative to the distal section 100 such that the proximal section 102 can be turned to drive the distal section 100 while the distal section 100 does not turn.

The diameter of the distal section 100 is approximately equal to the diameter of the large aperture 40 of the graft block 12. The tapered distal end 106 facilitates engagement of the pin with the aperture 40. If the graft block 20 is situated in the tunnel with the aperture axis partially out of alignment with the pin axis, the tapered distal end 106 and the chamfer 41 will engage one another and cause the graft block 12 to rotate about its axis to align the aperture 40 with the pin 14.

Figure 3:
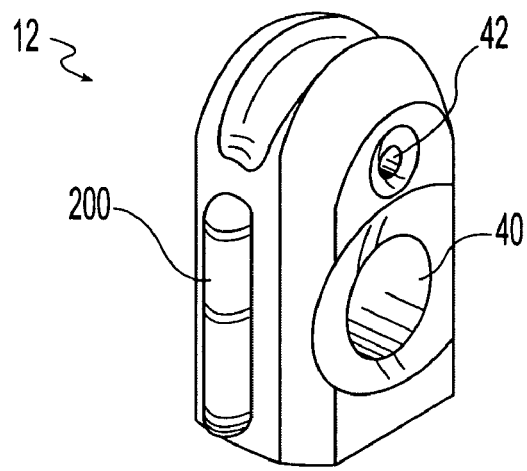
FIG. 3 is perspective view of an alternative embodiment of the graft block of FIG. 1.

FIG. 3 illustrates an alternative embodiment of the graft block 12 of FIG. 1 having a longitudinally extending radial projection 200. The projection 200 engages a slot or notch 202 previously formed in the wall of the bone tunnel at a known circumferential position such that the projection 200 is received in the slot 202 as the graft block 12 is inserted into the bone tunnel to align the aperture 40 with the transverse hole 64.

Figure 4:
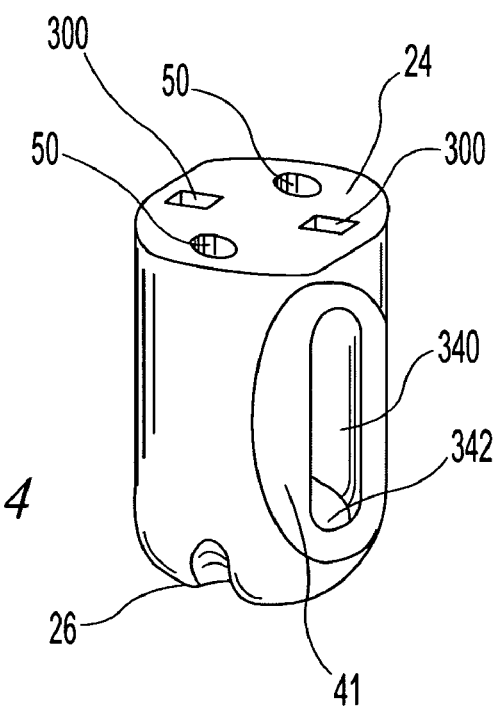
FIG. 4 is a perspective view of an alternative embodiment of the graft block of FIG. 1.

FIG. 4 illustrates an alternative embodiment of the graft block 12 of FIG. 1 having an optional keyway for engaging a rotationally rigid shaft shaped to fit the keyway. The keyway may have one or more openings. In the illustrative embodiment, the keyway comprises a pair of notches 300 that are adapted to receive a forked inserter (not shown) which has a gap between the forks to accommodate the graft 59 and/or intermediate connector. The engagement of the shaft and keyway maintains the graft block 12 in known rotational alignment with the shaft so that the shaft can be positioned to properly align the graft block 12 with the transverse hole 64. The illustrative embodiment of FIG. 4 also depicts an optional longitudinally elongated aperture 340. Such an elongated aperture 340 may be useful, for example, in a small diameter bone tunnel to facilitate a transverse member having a corresponding non-cylindrical cross-section to increase the strength of the transverse member without requiring a larger graft block diameter. For example, the cross-pin 14 of FIG. 1 may be made with a non-cylindrical distal section 100. This may be advantageously combined with the above described alternative cross-pin having a rotating junction between the proximal 102 and distal 100 sections. In this way, the proximal end 102 may be rotated while the non-cylindrical distal section progresses without rotation. Alternatively, a non-cylindrical cross-pin may be impacted or pressed into position. The non-cylindrical aperture of FIG. 4 may also be used with a transverse member having a round cross-section to permit the transverse member to engage the graft block even when there is some longitudinal misalignment of the graft block 12 with the transverse hole 64. The transverse member may pass through the aperture 340 proximal to the distal end 342 of the aperture. If so, when the graft 59 is tensioned, the graft block 12 will be pulled proximally until the distal end 342 engages the transverse member. The aperture 340 is chamfered 41 to also permit some rotational misalignment as described above.

Figure 5:
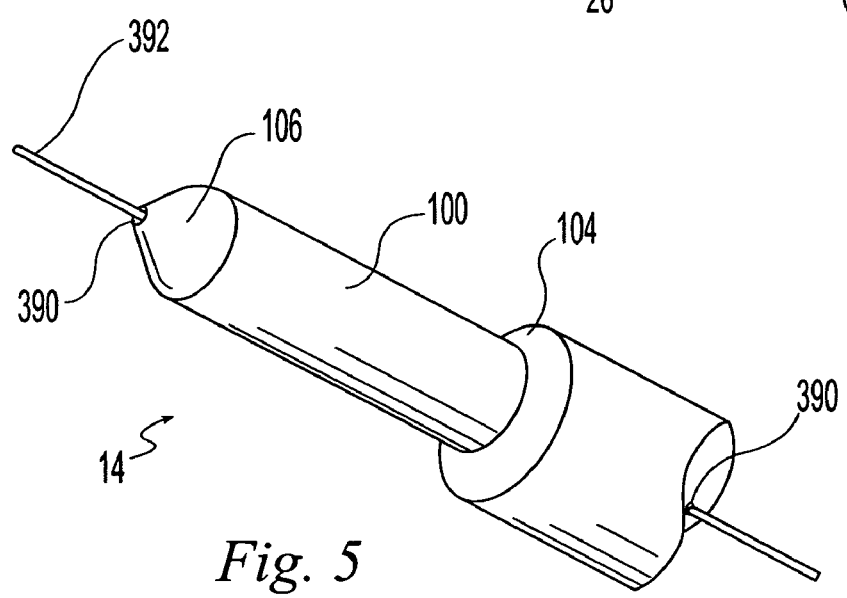
FIG. 5 is a perspective view of an alternative embodiment of the cross-pin of FIG. 1.

FIG. 5 illustrates an alternative embodiment of the cross-pin 14 of FIG. 1 having an optional longitudinal cannulation 390 to permit the cross-pin 14 to follow a guide wire 392 if desired.

Figure 6:
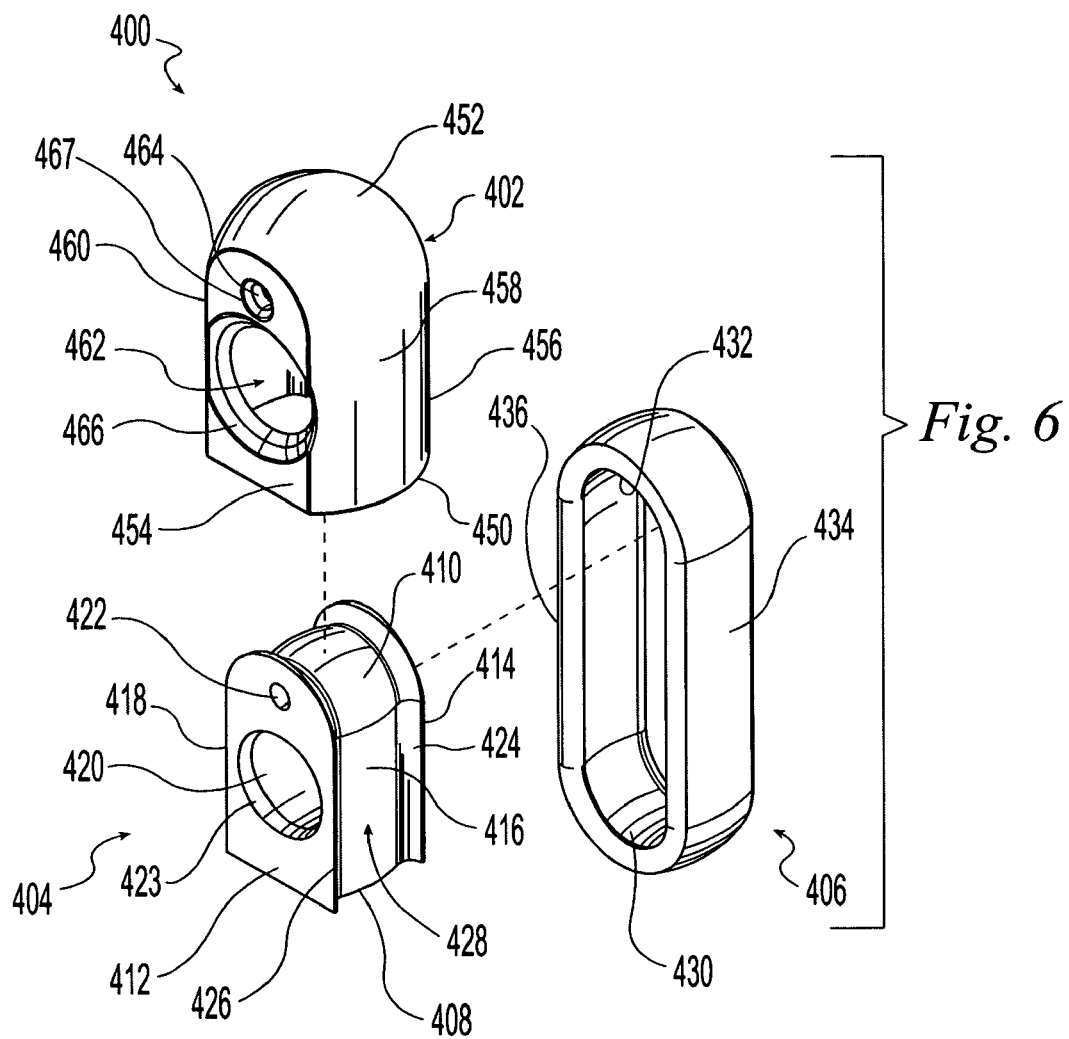
FIG. 6 is an exploded perspective view of an alternative embodiment of the graft block of FIG. 1.
Figure 7:
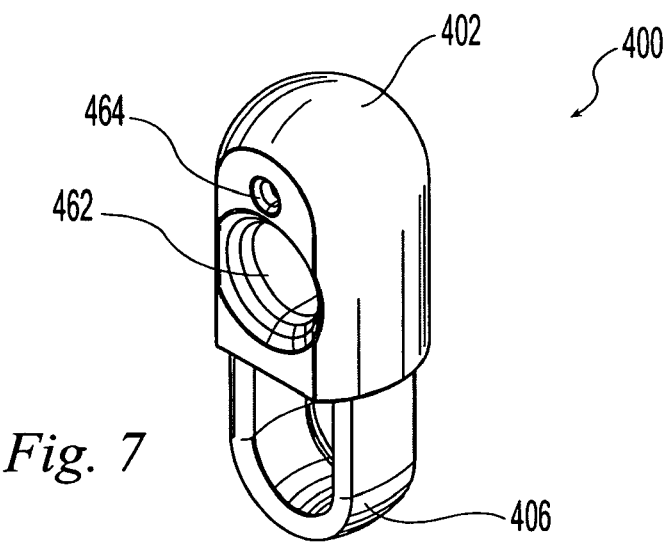
FIG. 7 is a perspective view of the graft block of FIG. 6.

FIGS. 6 and 7 illustrate an alternative embodiment of the graft block of FIG. 1 having a multi-piece construction. A graft block 400 comprises a cap 402, a core 404, and an intermediate connecting member 406 in the form of a loop. The core 404 includes a rectilinear body having a proximal end 408, a distal end 410, a pair of opposed parallel faces 412 and 414, and a pair of opposed parallel sides 416 and 418. Large 420 and small 422 transverse apertures extend through the body between the faces 412 and 414. The large 420 aperture is proximal of the small aperture 422 and includes a chamfer 423. A pair of projecting side walls 424 and 426 defines a U-shaped channel 428 along the exterior of the core 404 around the distal end and down the parallel sides 416 and 418. The intermediate connecting member 406 comprises a closed elongated loop having a proximal portion 430, a distal portion 432, and sides 434 and 436. The cap 402 includes a hollow rectilinear body having an open proximal end 450, a closed distal end 452, opposite parallel faces 454 and 456, and opposite parallel sides 458 and 460. Large 462 and small 464 transverse apertures extend through both faces 454 and 456. Chamfers 466 and 467 lead from each face 454 and 456 to the large 462 and small 464 apertures. The graft block 400 is assembled by placing the intermediate connector 406 on the core 404 within the U-shaped channel 428 with the distal portion 432 resting on the distal end 410 of the core 404 and the proximal portion 430 extending below the core. The core/connector assembly is inserted through the open proximal end 450 of the cap 402 until the distal end 410 of the core 404 is adjacent the distal end 452 of the cap 402 and the large 420 and small 422 core apertures align with the large 462 and small 464 cap apertures. The assembly may be secured by press fit, snap fit, adhesives, welding, solvent bonding, pinning, screwing, and/or other suitable means. Alternatively, the cap 402 can be molded over the core 404 and intermediate connector 406 or the cap 402 and core 404 can be molded as a single piece around the intermediate connector 406. When fully assembled, the cap covers the distal end 432 and sides 434 and 436 of the intermediate connector 406 such that it is securely retained and protected.

Figure 8:
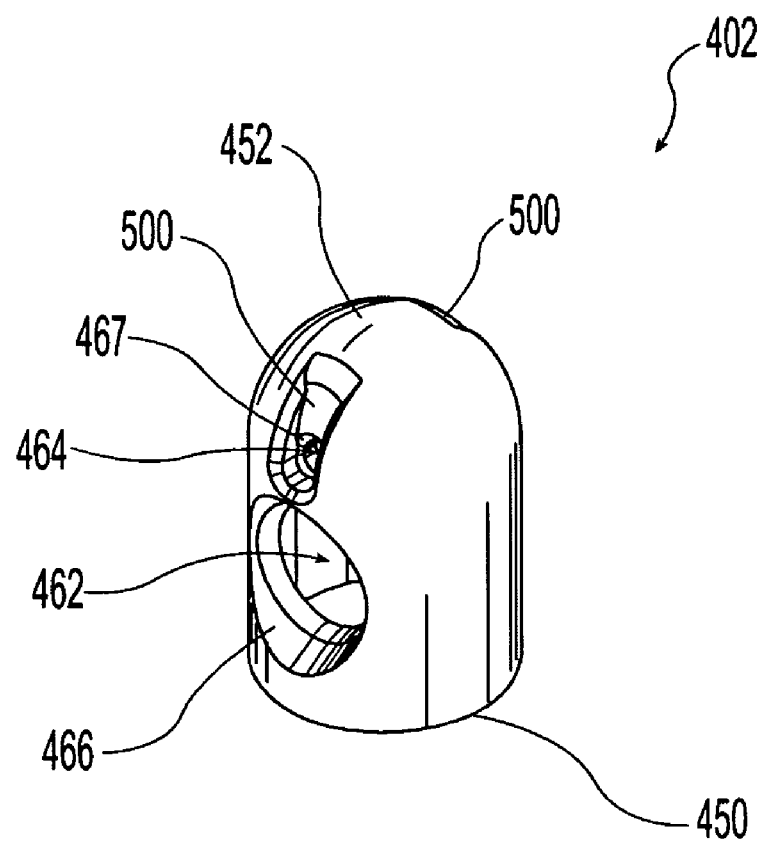
FIG. 8 is a perspective view of an alternative cap used in conjunction with the graft block of FIG. 6.
Figure 11:
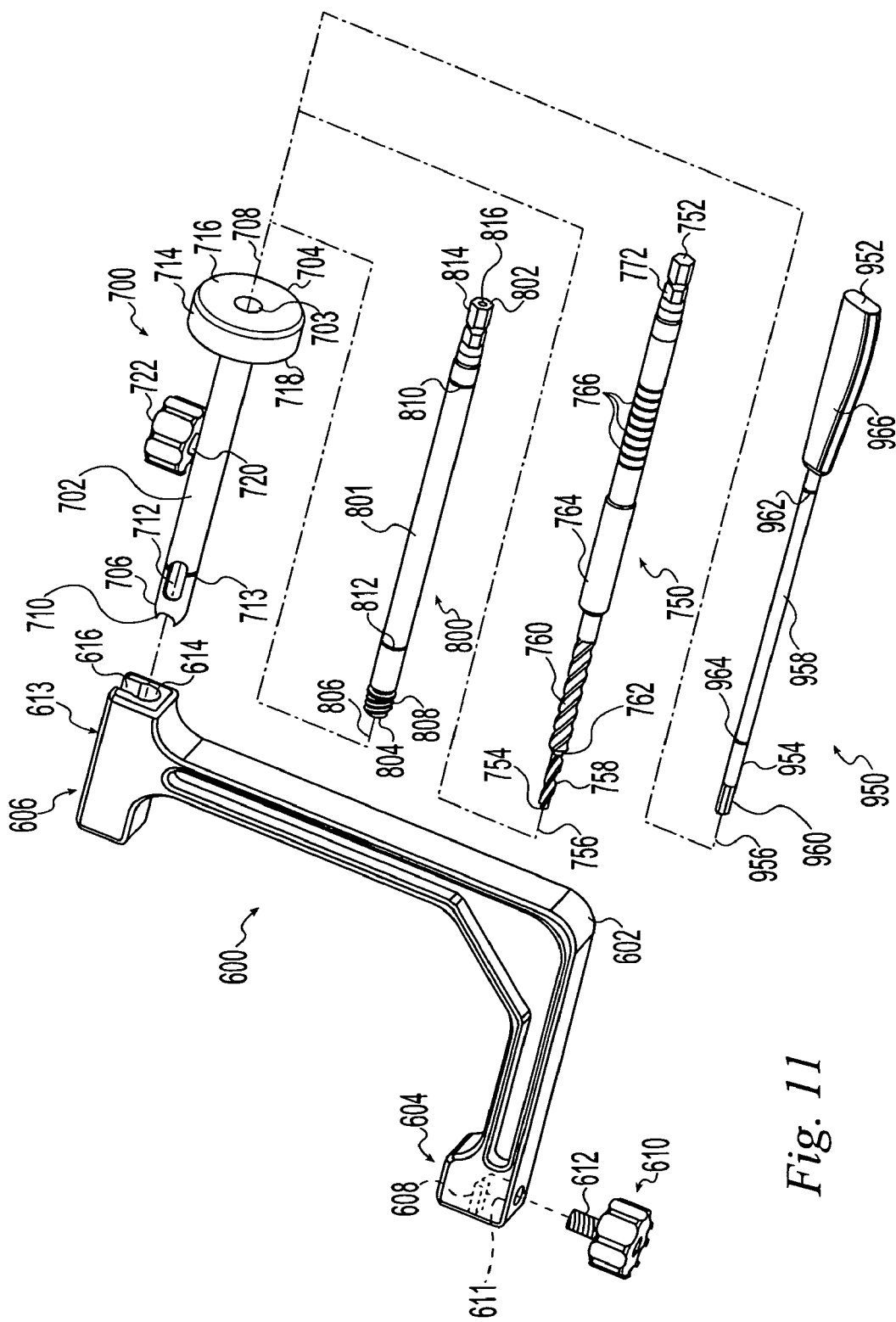

FIG. 8 depicts an alternative cap 402 having a cylindrical body without the faces 454 and 456 of FIG. 6. A pair of channels 500 lead from each end of the small aperture 464 toward the distal end 452 of the cap 402. The channels 500 receive the passing suture 65 to provide clearance between the cap 402 and bone tunnel.

FIGS. 9-20 depict an illustrative set of surgical instruments and their use in an illustrative surgical method to install the graft retaining system of FIGS. 1-8. Referring to FIGS. 9-14, the set of surgical instruments includes a tunnel drill bit 550, a transverse drill guide base 600, a tunnel guide rod 650, a drill sleeve 700, a transverse drill bit 750, a locator rod 800, a notch cutter 850, a suture passing pin 900, and a driver 950.

Figure 15:
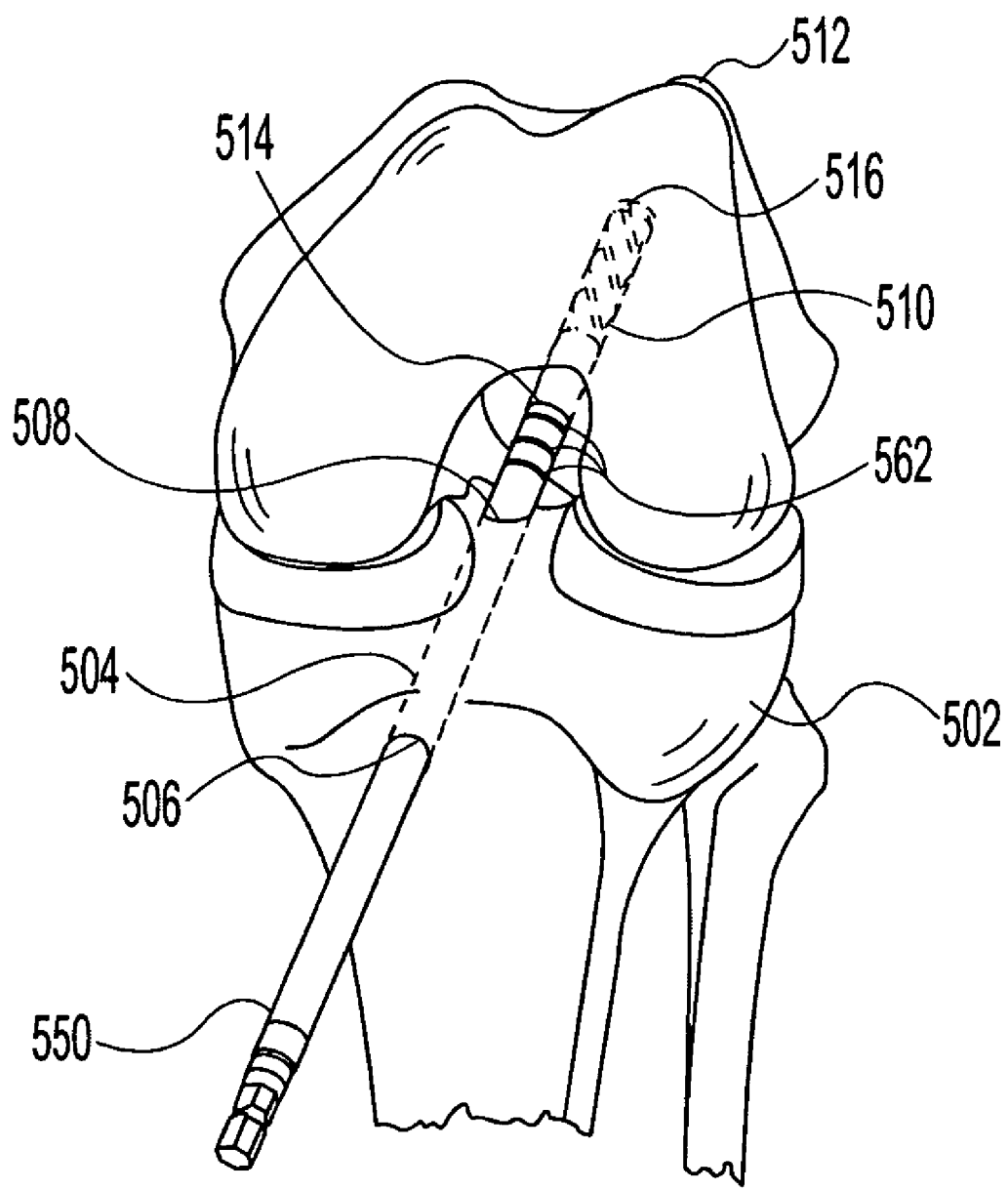
FIGS. 15-20 are perspective views of a human knee joint showing an illustrative method of using the instruments of FIGS. 9-11.

The tunnel drill bit 550 includes a cylindrical body 552 having a proximal end 554, a distal end 556, and an axis 558 extending therebetween. Cutting flutes 560 are formed adjacent the distal end 556 to cut into the bone to form tibial and femoral bone tunnels 504, 510 (FIG. 15). Depth markings 562 on the body 552 can be viewed intraoperatively within the joint to determine the depth of the femoral bone tunnel 510. A driver engagement 564 is formed near the proximal end 554 to permit the tunnel drill bit 550 to be easily connected to a powered drill or other driver. A plurality of tunnel drill bits 550 having different diameters is provided so that the bone tunnels 504, 510 may be matched to the graft 59 (FIG. 1) size for a close fit between the graft 59 and tunnels 504, 510.

The base 600 includes an "L"-shaped body 602 providing a rigid mounting for the instruments. The base 600 has a rod interface 604 at one end and a sleeve interface 606 at an opposite end. The rod interface 604 includes a lug receiving slot 608 and a locking bolt 610. A hole 611 in the rod interface 604 communicates with the lug receiving slot 608 and is threaded to receive the locking bolt 610 such that an end 612 of the locking bolt is positionable in the lug receiving slot 608. The sleeve interface 606 includes an outer surface 613, a longitudinal throughbore 614, and a longitudinal throughslot 616 along one side of the bore 614 communicating from the bore 614 to the outer surface 613. The slot 616 is slightly narrower than the bore 614 diameter such that the bore 614 and slot 616 form a longitudinal keyhole aperture open on one side.

The tunnel guide rod 650 references the bone tunnels 504, 510 to help align the base 600 and other instruments. The tunnel guide rod 650 includes a cylindrical rod body 652 having a cylindrical outer wall, a proximal end 654, a distal end 656, and an axis 658 extending therebetween. The rod body 652 includes a first longitudinal cannula 660 extending along the axis 658 from the proximal end 654 to the distal end 656. A second longitudinal cannula 662 is radially offset from the first cannula 660 and extends parallel to the first cannula 660 from the proximal end 654 to the distal end 656 for receiving the notch cutter 850. The second cannula 662 is radially offset such that a chord 664 of the cannula 662 intersects the outer wall of the rod body 652. This intersection creates an outwardly opening slot 665. The tunnel guide rod 650 includes a transverse through bore 668 spaced a predetermined distance from the distal end 656. The outwardly opening slot 665 is oriented at a predetermined circumferential position relative to the transverse bore 668 corresponding to the position of the radial projection 200 of the graft block 12 relative to the aperture 40 (FIG. 3). In the illustrative embodiments, the slot 665 and projection 200 are oriented perpendicular to the transverse bore 668 and aperture 40. Depth markings 670 are formed on the rod body 652. the depth markings 670 correspond to the depth markings 562 on the tunnel drill bit 550. A transverse attachment lug 672 is positioned near the proximal end 654. The attachment lug 672 is receivable by the lug receiving slot 608 of the rod interface 604 on the drill guide base 600. With the attachment lug 672 seated in the lug receiving slot, the locking bolt 610 can be tightened against the attachment lug 672 to attach the tunnel guide rod 650 to the drill guide base 600. A plurality of positioning rods 650 having different diameters is provided to match the tunnel drill bit 550 diameters.

The drill sleeve 700 includes a hollow, cylindrical barrel 702 having a cylindrical outer wall, a proximal end 704, a distal end 706 and a longitudinal axis 708 therebetween. The barrel 702 is open both proximally and distally to provide an elongated portal 703 from the proximal end 704 to the distal end 706. Teeth 710 are formed at the distal end 706, for example by cutting scallops across the distal end 706, to facilitate the distal end 706 gripping a bone surface. A window 712 for viewing implants and instruments passed through the portal 703 is formed in the side of the barrel 702 communicating from the outer wall to the portal 703. A depth marking 713 is formed on the outer wall of the drill sleeve 700 adjacent the window 712 to provide a depth reference for instruments and implants passed through the portal 703. An enlarged ring 714 is formed near the proximal end 704 to provide an enlarged gripping surface. The ring 714 has an outer diameter larger than the outer diameter of the barrel 702. The ring 714 includes planar proximal 716 and distal 718 surfaces. The proximal surface 716 may also be used to provide a depth reference for instruments and implants passed through the portal 703. A locking bolt 720 projects radially from the outer wall of the barrel 702 and threadably receives a locking nut 722. The barrel 702 is sized to slide into the sleeve interface 606 through bore 614 where it is constrained to axial translation along the bore 614. The barrel 702 is larger than the slot 616 so that the barrel cannot fit radially through the slot 616. The slot 616 receives the bolt 720 in sliding relationship. The drill sleeve 700 can be positioned within the bore 614 at a desired location and then locked in place by tightening the locking nut 722 against the outer surface 613 of the sleeve interface 606.

With the positioning rod 650 assembled to the rod interface 604 and the drill sleeve 700 assembled to the sleeve interface 606, the barrel 702 portal 703 is aligned with the transverse throughbore 668 in the positioning rod 650. Thus, instruments and implants passed through the drill sleeve 700 may be directed toward and/or through the transverse bore 668.

The transverse drill bit 750 includes a proximal end 752, a distal end 754, and a longitudinal axis 756 therebetween. The transverse drill bit 750 is guided by the drill sleeve 700 to form the transverse bone hole 64 (FIG. 16) intersecting the bone tunnel 510. A first drilling portion 758 is formed adjacent the distal end 754. The first drilling portion 758 corresponds to a predetermined hole size for receiving the distal cylindrical section 100 of the cross-pin 14. A second drilling portion 760 is formed between the first drilling portion 758 and the proximal end 752. The second drilling portion 760 has a larger diameter than the first drilling portion 758 that corresponds to a predetermined hole size for receiving the proximal cylindrical section 102 of the cross-pin 14. A tapered shoulder 762 transitions between the first 758 and second 760 drilling portions. The drill bit 750 includes a smooth cylindrical bearing portion 764 between the second drilling portion 760 and the proximal end 752. The bearing portion 764 has a diameter sized to fit the internal diameter of the drill sleeve 700 portal 703 in smooth rotational and axial sliding engagement. The drill bit 750 includes a plurality of depth markings 766. With the drill bit 750 positioned within the drill sleeve 700, the depth markings 766 may be read adjacent the proximal surface 716 of the ring 714. The depth markings 766 are calibrated to indicate the distance from the drill bit shoulder 762 to the distal end 706 of the drill sleeve 700. A driver engagement 772 formed at the proximal end 752 allows quick coupling to a driver for turning the drill bit 750.

The locator rod 800 includes a cylindrical body 801, a proximal end 802, a distal end 804, and an axis 806 extending therebetween. The cylindrical body 801 is a close sliding fit within the drill sleeve 700 but it will pass radially through the slot 616 of the sleeve interface 606. The locator rod 800 includes threads 808 formed adjacent the distal end 804. The threads 808 are sized to engage the transverse bone hole 64 formed by the second drilling portion 760 of the transverse drill bit 750. The locator rod 800 includes proximal 810 and distal 812 depth markings. The proximal depth marking 810 aligns with the proximal surface 716 of the drill sleeve 700 ring 714 and the distal depth marking 812 aligns with the depth marking 713 adjacent the drill sleeve 700 window 712 when the locator rod 800 is fully engaged in the transverse bone hole 64 as measured relative to the distal end 706 of the drill sleeve 700. The locator rod 800 includes a driver engagement 814 formed at the proximal end 802 that allows quick coupling to a driver or handle for turning the locator rod 800 into the bone. The illustrative locator rod 800 includes an optional axial lumen 816 for receiving an arthroscope. This lumen 816 permits examination of the transverse bone hole 64 and/or viewing of the orientation of the graft block 12 relative to the transverse bone hole 64 while the locator rod 800 is engaging the transverse bone hole 64.

The notch cutter 850 includes a proximal end 852, a distal end 854, and a longitudinal axis 856 therebetween. A cylindrical shaft 858 extends from the distal end 854 toward the proximal end 852. A cutter tooth 860 in the general form of a rectangular prism projects radially from the cutter shaft 858 near the distal end 854. The cutter tooth 860 has a sharpened distal edge 864. The cylindrical shaft 858 is sized to slide within the second cannula 662 in the tunnel guide rod 650 with the cutter tooth 860 projecting radially outwardly through the outwardly opening slot 665. A handle 868 is formed adjacent the proximal end 852 of the notch cutter 850.

The suture passing pin 900 includes a cylindrical body 901 having a proximal end 902, a distal end 904, and a longitudinal axis 906 extending therebetween. A sharpened tip 908 at the distal end facilitates driving the pin through bone to form a suture hole. An eyelet 910 formed at the proximal end 902 receives a suture to be pulled through the suture hole formed by the pin 900.

The driver 950 includes a proximal end 952, a distal end 954, and an axis 956 therebetween. A cylindrical shaft 958 extends from the distal end 954 toward the proximal end 952 and a handle 966. An engagement tip 960 is formed adjacent the distal end 954 and is shaped to engage the drive recess 112 of the cross-pin 14 (FIG. 1). The driver 950 includes proximal 962 and distal 964 depth markings. The proximal depth marking 962 aligns with the proximal surface 716 of the drill sleeve 700 ring 714 and the distal depth marking 964 aligns with the depth marking 713 adjacent the drill sleeve 700 window 712 when the driver 950 engages the cross-pin 14 and the cross-pin 14 is counter sunk to a desired level relative to the distal end 706 of the drill sleeve 700.

The use of the illustrative instruments of FIGS. 9-14 is shown in FIGS. 15-20. A suitable graft 59 is prepared and connected to the graft block 12. For example a semitendinosus or gracilis tendon is harvested and connected to the graft block 12 via the retaining loop 16. The graft block 12 is chosen to match the diameter of the graft 59. A bone tunnel drill bit 550 is chosen with a diameter that will form a tunnel that closely fits the graft 59/graft block 12 assembly. A bone tunnel 504 is drilled through the tibia 502 from a first end 506 to a second end 508. The tunnel drill bit 550 is advanced further to drill a tunnel 510 into the femur 512 from a first end 514 to a second end 516, in line with the tibial tunnel 504 as shown in FIG. 15. Alternatively, the femoral tunnel 510 can be drilled through a medial portal in the knee joint and need not necessarily align with the tibial tunnel 504. The depth of the femoral tunnel 510 from the first end 514 to the second end 516 is measured by reading the depth from the depth markings 562 on the tunnel drill bit 550 while it is fully seated against the second end 516 of the tunnel 510. The tunnel drill 550 bit is removed and the depth of the femoral bone tunnel 510 is marked 518 on the graft 59/graft block 12 assembly as measured from the distal end of the assembly. The mark 518 (FIG. 18) will serve as an indicator of when the graft block 12 is fully seated in the bone tunnel.

Figure 16:
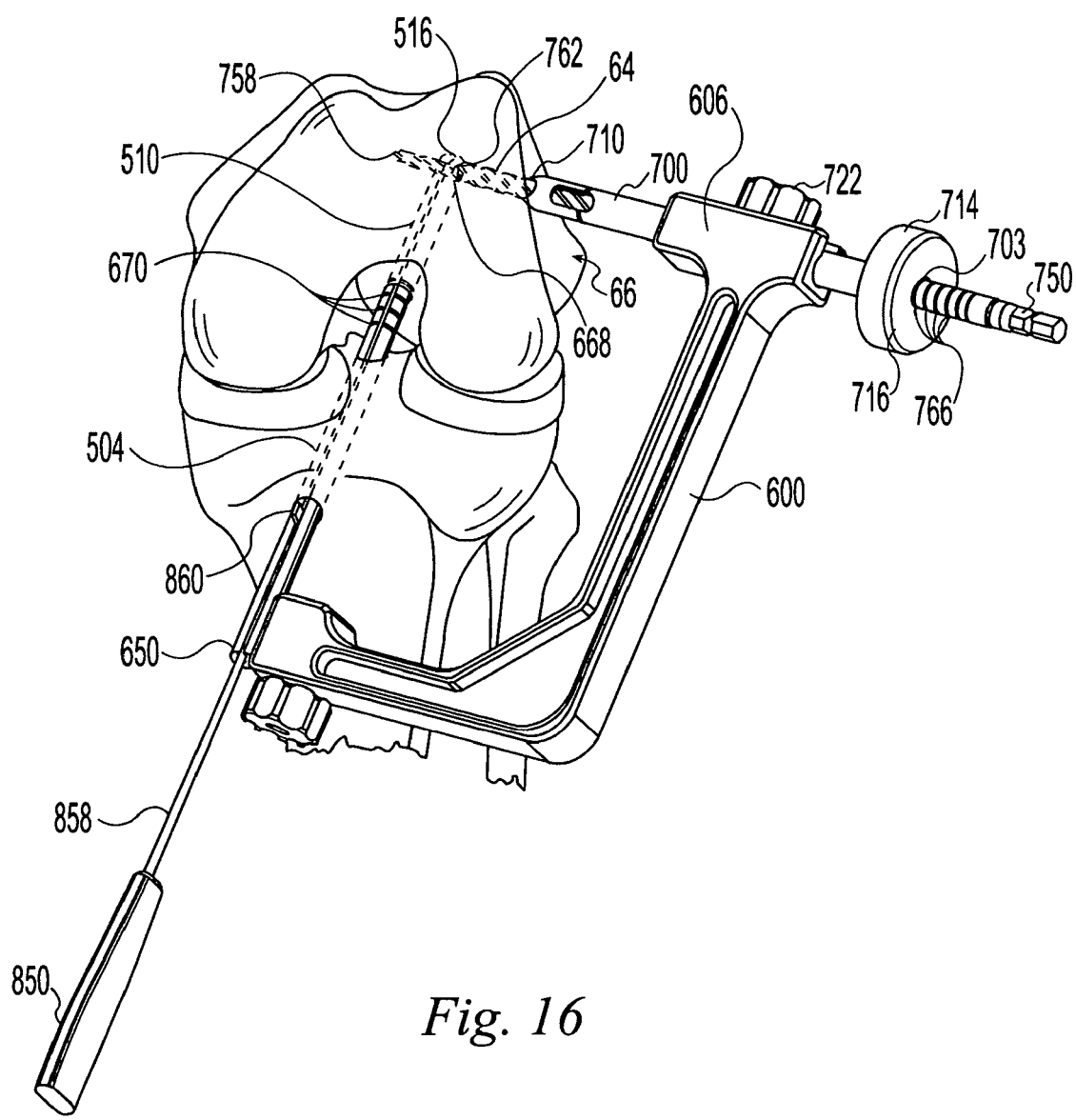

A tunnel guide rod 650 is selected having a diameter corresponding to a desired fit within the bone tunnels 504, 510. The tunnel guide rod 650 is assembled to the drill guide base 600 and then inserted through the tibial 504 and femoral 510 bone tunnels and seated against the second end 516 of the femoral bone tunnel 510 as shown in FIG. 16. Alternatively, if the femoral tunnel 510 was formed through a medial portal, the femoral positioning rod 650 is inserted through the medial portal and into the femoral tunnel 510. The user can verify that the tunnel guide rod 650 is fully seated by referring to the depth marks 670. Seating is confirmed if the indicated femoral tunnel 510 depth corresponds to the depth measured during drilling. The drill sleeve 700 is inserted through the sleeve interface 606 and through a skin incision until the drill sleeve 700 teeth 710 grip the anterolateral femoral cortex 66. The drill sleeve 700 is then locked in place by tightening the locking nut 722.

The transverse drill bit 750 is inserted through the sleeve 700 portal 703 and activated to drill a transverse hole 64 from the anterolateral femoral cortex 66 to intersect the femoral bone tunnel 510. The distal drilling portion 758 passes through the transverse bore 668 of the tunnel guide rod 650 and on into the femur on the opposite side of the femoral bone tunnel 510. The shoulder 762 will eventually seat against the femoral guide rod 650 at the transverse bore 668 and halt the progress of the drill bit 750. With the shoulder 762 seated, the distance from the shoulder 762 to the anterolateral femoral cortex 66 can be read by noting which depth marking 766 on the transverse drill bit 750 is adjacent the proximal surface 716 of the enlarged ring 714. This depth measurement is then used to select a cross-pin 14 having a proximal length that will allow it to seated against the graft block 12 and extend to a desired position near the anterolateral femoral cortex 66. It is advantageous for the transverse pin 14 to reach a position near the anterolateral femoral cortex 66, but not project from it.

Figure 17:
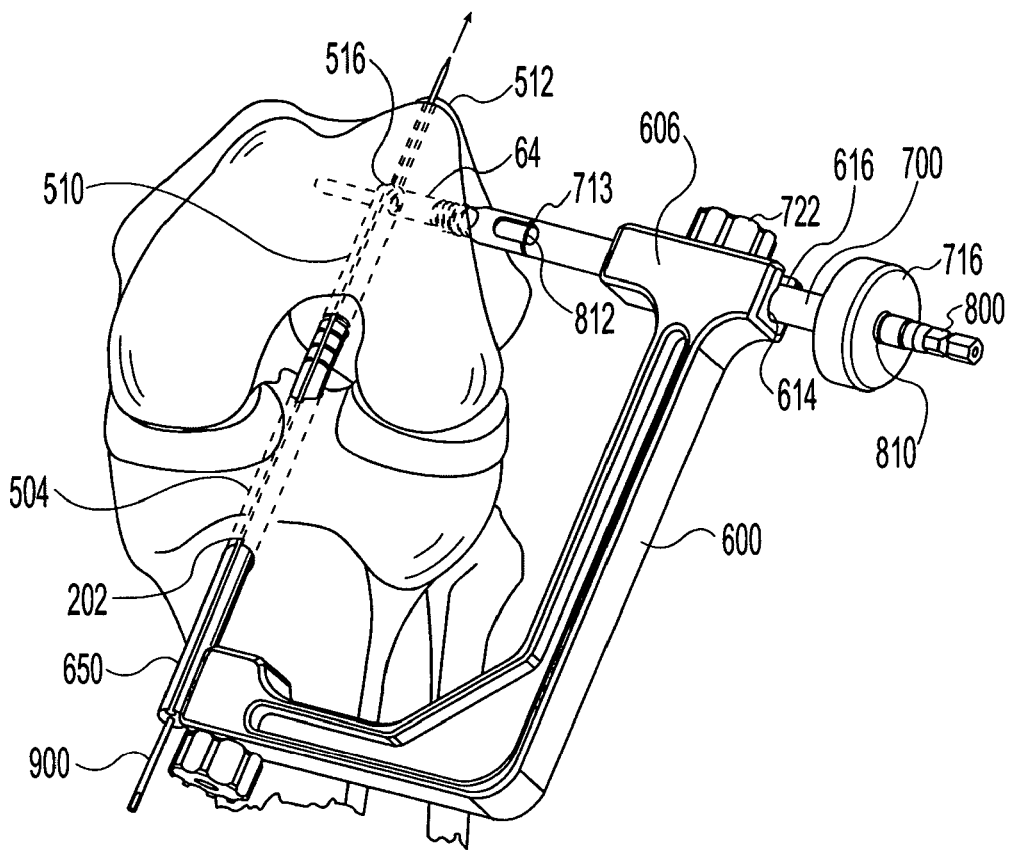

If the graft block 12 of FIG. 3 is being used, the radial notch 202 is formed to receive the radial projection 200 of the graft block 12. The transverse drill bit 750 may be left in place to help hold the drill guide in position or it may be removed and replaced with the locator rod 800. The notch cutter 850 shaft 858 is inserted into the second cannula 662 of the tunnel guide rod 650 with the cutter tooth 860 projecting through the longitudinal slot 665. The notch cutter 850 is pushed distally so that the cutting edge 864 of the cutter tooth 860 engages the bone and forms the notch 202 in the walls of the bone tunnels 504, 510. The notch cutter 850 is removed. If the transverse drill bit 750 was not removed before forming the notch 202, it is now removed from the drill sleeve 700 and the locator rod 800 is inserted through the drill sleeve 700 and threaded into the transverse hole 64 until the threads 808 are fully engaged in the bone as shown in FIG. 17.

Figure 18:
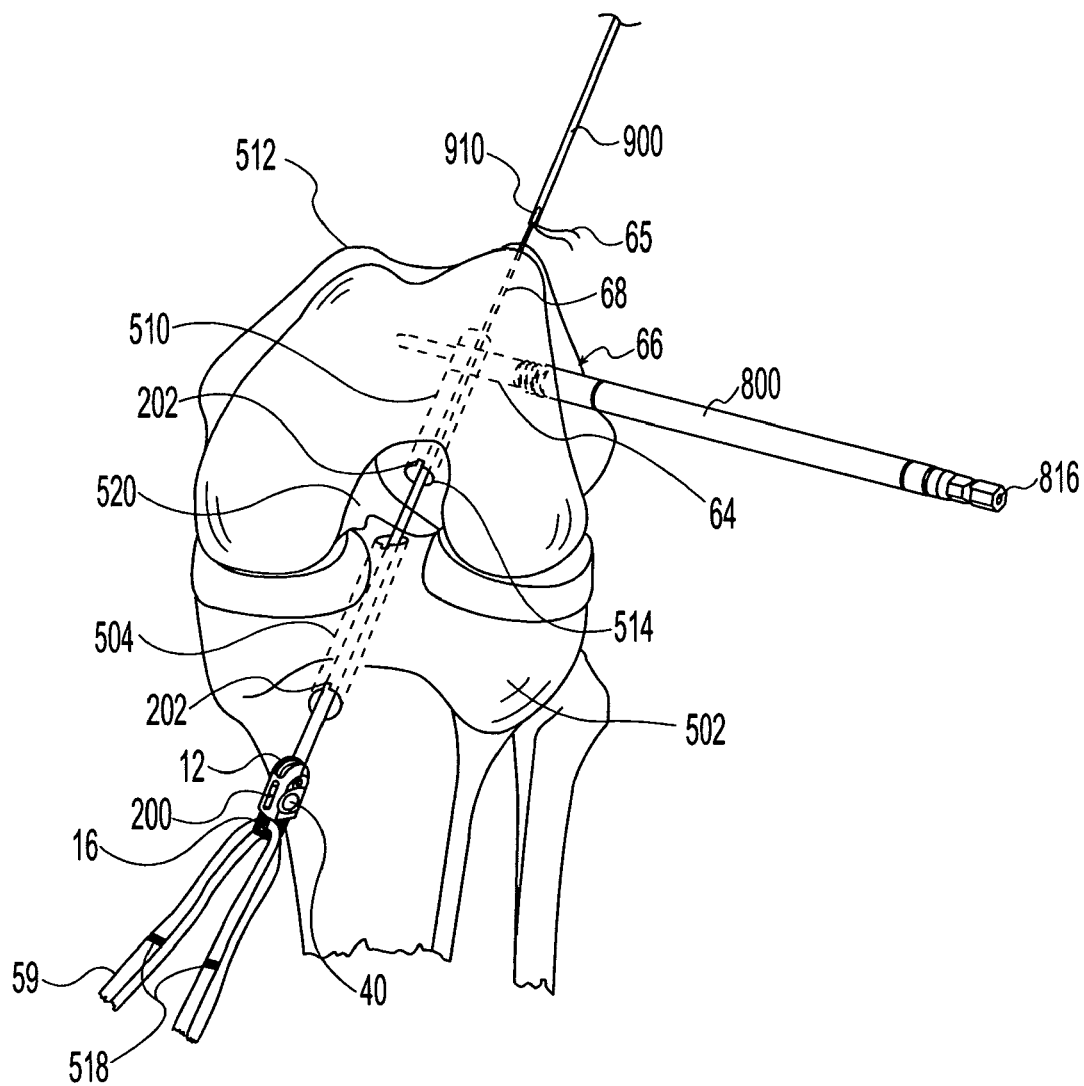

The suture passing pin 900 is inserted into the first cannula 660 and is driven until it is embedded in the femur 512 beyond the second end 516 of the femoral bone tunnel 510. The drill sleeve 700 locking nut 722 is loosened and the drill sleeve 700 is slid out of the axial bore 614 and off of the locator rod 800. The femoral guide rod 650 and drill guide base 600 are removed by displacing the base 600 proximally and sliding the sleeve interface 606 slot 616 over the locator rod 800 and the femoral guide rod 650 out of the bone tunnels 504, 510. The locator rod 800 maintains access through the surrounding soft tissue to the transverse bone hole 64 and allows easy subsequent repositioning of the drill sleeve 700 as shown in FIG. 18.

Figure 19:
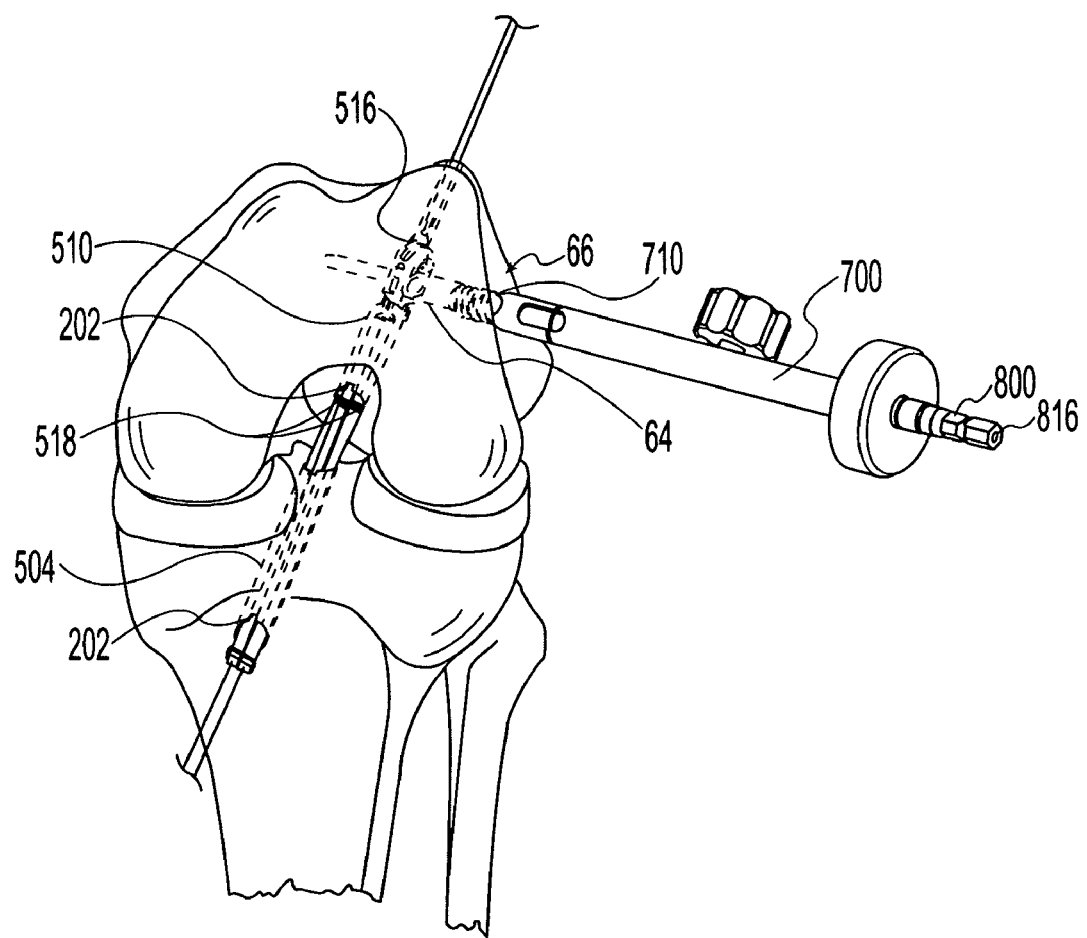
Figure 20:
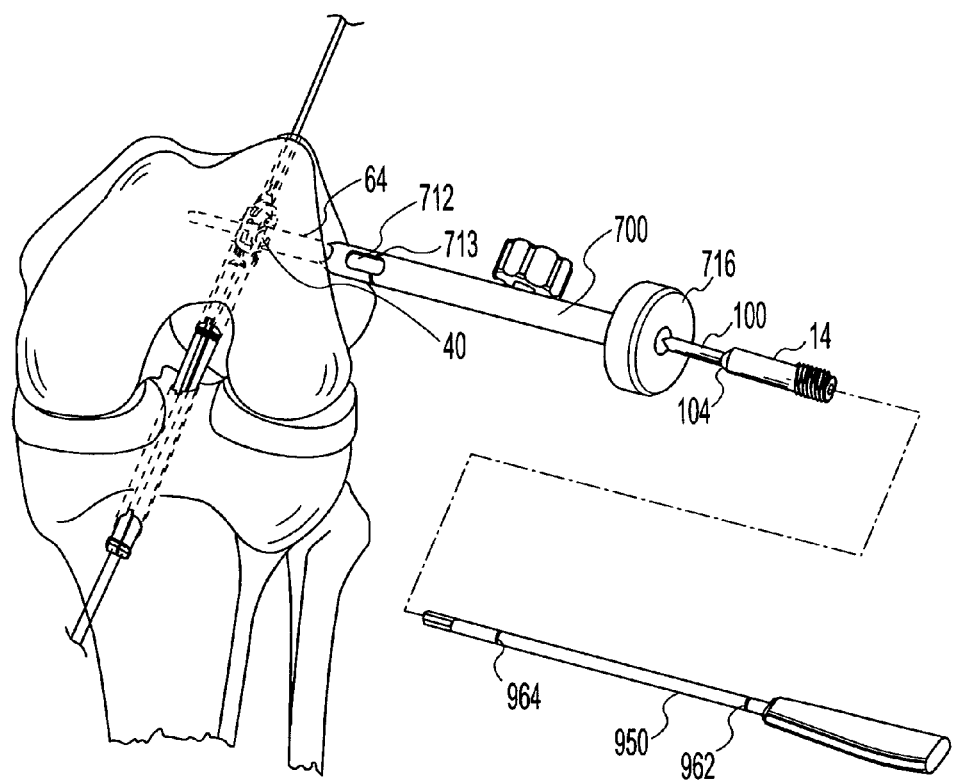

The graft block 12 suture 65 is threaded through the eye 910 of the suture passing pin 900 and the suture passing pin 900 is advanced to form the suture tunnel 68 through the femur out through the anterolateral femoral cortex 66, and adjacent to or through the quadriceps muscle. Pulling the suture passing pin 900 through the suture tunnel 68 pulls the suture 65 through the tibia 502 and the femur 512. If present, the radial projection 200 is aligned with the tibial tunnel 504 notch 202 cut in the tunnel 504 sidewall. The suture 65 is pulled to advance the graft block 12 into the joint space 520. The graft block 12 is rotationally aligned so that its aperture 40 is aligned with the transverse bone hole 64. If present, the radial projection 200 is aligned with the notch 202 in the femoral bone tunnel 510. The suture 65 is pulled to seat the graft block 12 in the femoral bone tunnel 510. Optionally, seating can be checked by viewing the mark 518 relative to the femoral bone tunnel 510 first end 514. Seating is verified if the mark 518 is adjacent the first end 514. Also optionally, an arthroscope can be directed down the locator rod 800 lumen 816 to verify the alignment of the graft block 12 relative to the transverse bone hole 64. The drill sleeve 700 is now replaced over the locator rod 800 until its teeth 710 bite into the anterolateral femoral cortex 66 as shown in FIG. 19. The locator rod 800 is removed by unscrewing it from the transverse bone hole 64. Optionally, an arthroscope may be inserted into the drill sleeve 700 to verify the alignment of the graft block 12.

The cross-pin 14 is advanced through the drill sleeve 700 (FIG. 20) and into the transverse hole 64 until the first cylindrical portion 100 of the cross-pin 14 passes through the large aperture 40 of the graft block and into the femur on the opposite side thus securing the graft 59/graft block 12 assembly in the bone tunnel 510. The graft block 12 aperture 40 only needs to be in general alignment with the transverse hole 64 prior to passing the graft block 12 into the bone tunnel. Once the graft block 12 is seated in the bone tunnel 510, the cross-pin 14 is advanced to secure the graft block 12 in the tunnel 510. Because of the chamfered 41 entrance of the aperture 40 and the taper 106 on the pin 14, the pin 14 can engage the graft block 12 such that even if there is some misalignment, the graft block 12 will rotate into alignment with the cross-pin 14. The cross-pin 14 may be advanced until the transition section 104 seats against the chamfered entrance 41 of the aperture 40. Alternatively, the cross-pin 14 may be advanced until the proximal depth markings 962, 964 on the driver align with the proximal surface 716 of the drill sleeve 700 and window 712 depth marking 713 respectively. The depth markings are arranged so that when they are aligned, the proximal end 110 of the cross-pin 14 is countersunk a desired amount beyond the distal end 706 of the drill sleeve 700.

Figure 21:
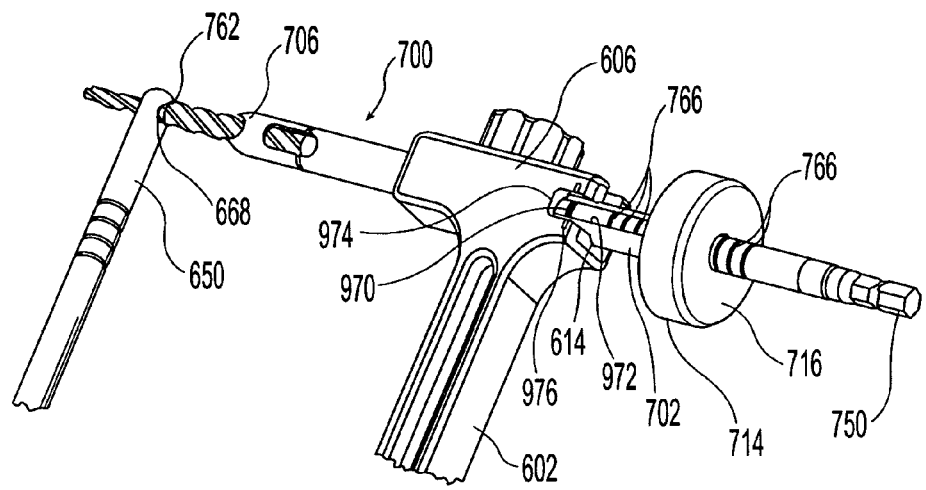
FIG. 21 is a perspective view of the assembled instruments of FIGS. 9-11 showing an alternative transverse depth measuring arrangement.

FIG. 21 shows an alternative illustrative depth gauging arrangement for drilling the transverse bone hole 64. In this embodiment, the transverse drill bit 750 includes a drill stop mark 970 distal to the plurality of depth markings 766. The drill sleeve 700 includes an elongated proximal window 972 extending through the side of the drill sleeve barrel 702 to communicate with the drill sleeve portal 703. This window 972 permits visualization of the drill stop mark 970 on the transverse drill bit 750. The sleeve interface 606 of the "L"-shaped body 602 includes a notch 974 adjacent the elongated through bore 614. Drill stop lines 976 are formed on the sleeve interface 606 adjacent the notch 974. In use, the tunnel guide rod 650 is inserted into the femoral bone tunnel 510 and the distal end 706 of the drill sleeve 700 is positioned against the anterolateral femoral cortex 66. The notch 974 in the sleeve interface 606 permits visualization of the drill stop mark 970 even if the ring 714 of the drill sleeve 700 is seated against the sleeve interface 606 as may occur in the case of a small bone. The transverse drill bit 750 is placed in the drill sleeve 700 and drilled into the femur until the drill stop mark 970 aligns with the drill stop lines 976 within the notch 974. The drill stop lines 976 are in a fixed position on the sleeve interface 606 which is in a known fixed position relative to the tunnel guide rod 650. Thus, aligning the drill stop mark 970 with the drill stop lines 976 positions the transverse drill at a predetermined depth relative to the tunnel guide rod 650. The use of the drill stop mark 970 provides an alternative to the transverse drill bit 750 shoulder 762 bottoming on the tunnel guide rod 650 to establish proper transverse bone hole 64 depth. The drill stop mark 970 is positioned so that the shoulder 762 stops just short of bottoming on the femoral positioning rod 650. The shoulder 762 then acts as a secondary stop if the transverse drill 750 is inadvertently advanced past the drill stop mark 970. The distance from the shoulder 762 to the anterolateral femoral cortex 66 is then read by noting which depth marking 766 on the transverse drill bit 750 is adjacent the proximal surface 716 of the ring 714 as before. This distance measurement is a guide to selecting the appropriate length transverse pin 14.

Figure 22:
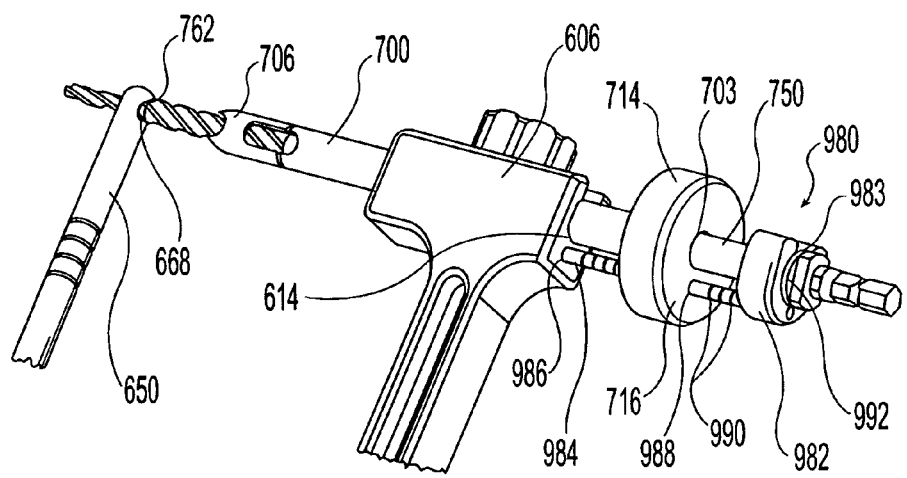
FIG. 22 is a perspective view of the assembled instruments of FIGS. 9-11 showing an alternative transverse depth measuring arrangement.

FIG. 22 shows another alternative illustrative depth gauging arrangement for drilling the transverse bone hole 64. In this embodiment, a depth stop 980 is mounted on the sleeve interface 606 and projects proximally. The depth stop 980 includes a stop body 982 having a "U"-shaped opening 983 for receiving the transverse drill bit 750. A support rod 984 connects the stop body 982 to the sleeve interface 606. One end of the support rod 984 is fixed to the stop body 982 and the other end is releasably received by a socket 986 in the sleeve interface 606 below the longitudinal through bore 614. The enlarged ring 714 of the drill sleeve 700 includes a through hole 988 below the elongated portal 703 for the support rod 984 to pass through. Graduations 990 are formed at intervals along the support rod 984. The transverse drill bit 750, includes a stop collar 992 near its proximal end. In use, the drill sleeve 700 is engaged with the sleeve interface 606. The depth stop 980 is mounted by inserting the support rod 984 through the hole 988 in the ring 714 of the drill sleeve 700 and into engagement with the socket 986 of the sleeve interface 606. The tunnel guide rod 650 is inserted into the femoral bone tunnel 510 and the distal end 706 of the drill sleeve 700 is positioned against the anterolateral femoral cortex 66. The transverse drill bit 750 is placed in the drill sleeve 700 and drilled into the femur until the stop collar 992 abuts the depth stop 980. The depth stop 980 is connected to a fixed position on the sleeve interface 606 which is in a known fixed position relative to the tunnel guide rod 650. Thus, using the depth stop 980 positions the transverse drill at a predetermined depth relative to the tunnel guide rod 650. The use of the depth stop 980 provides an alternative to the transverse drill bit 750 shoulder 762 bottoming on the tunnel guide rod 650 to establish proper transverse bone hole 64 depth. The distance from the shoulder 762 to the anterolateral femoral cortex 66 is then read by noting which graduation 990 on the support rod 984 is adjacent the proximal surface 716 of the ring 714. This distance measurement is a guide to selecting the appropriate length transverse pin 14.

Figure 23:
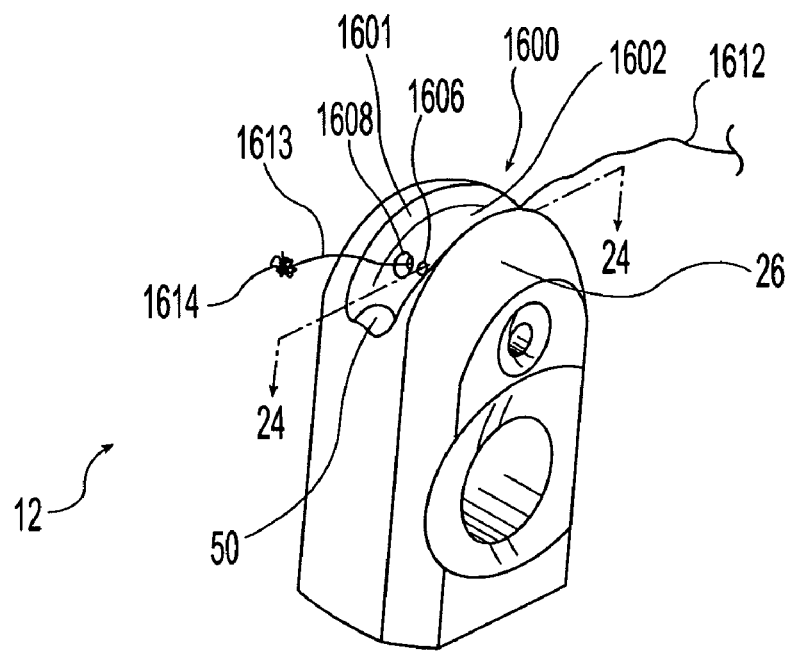
FIG. 23 is a perspective view of the graft block of FIG. 1 showing an optional loop attachment mechanism.
Figure 24:
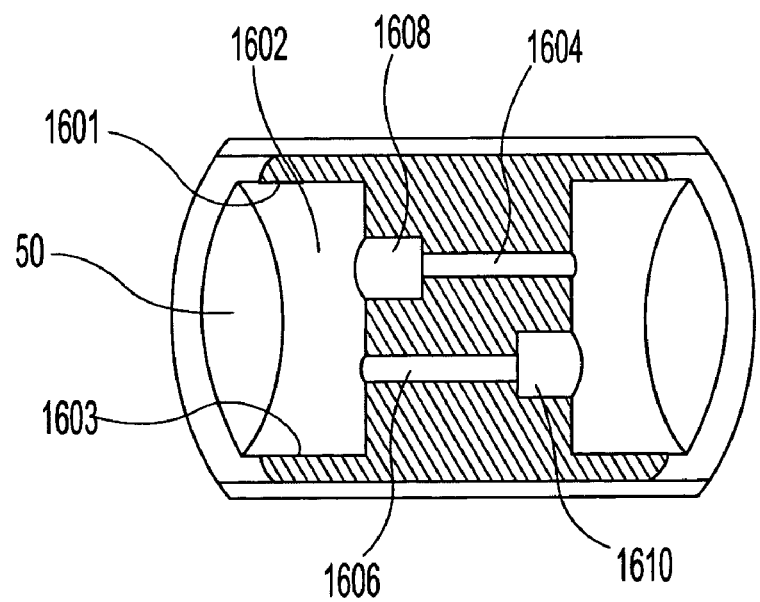
FIG. 24 is a section view taken along line 24-24 of FIG. 23.
Figure 25:
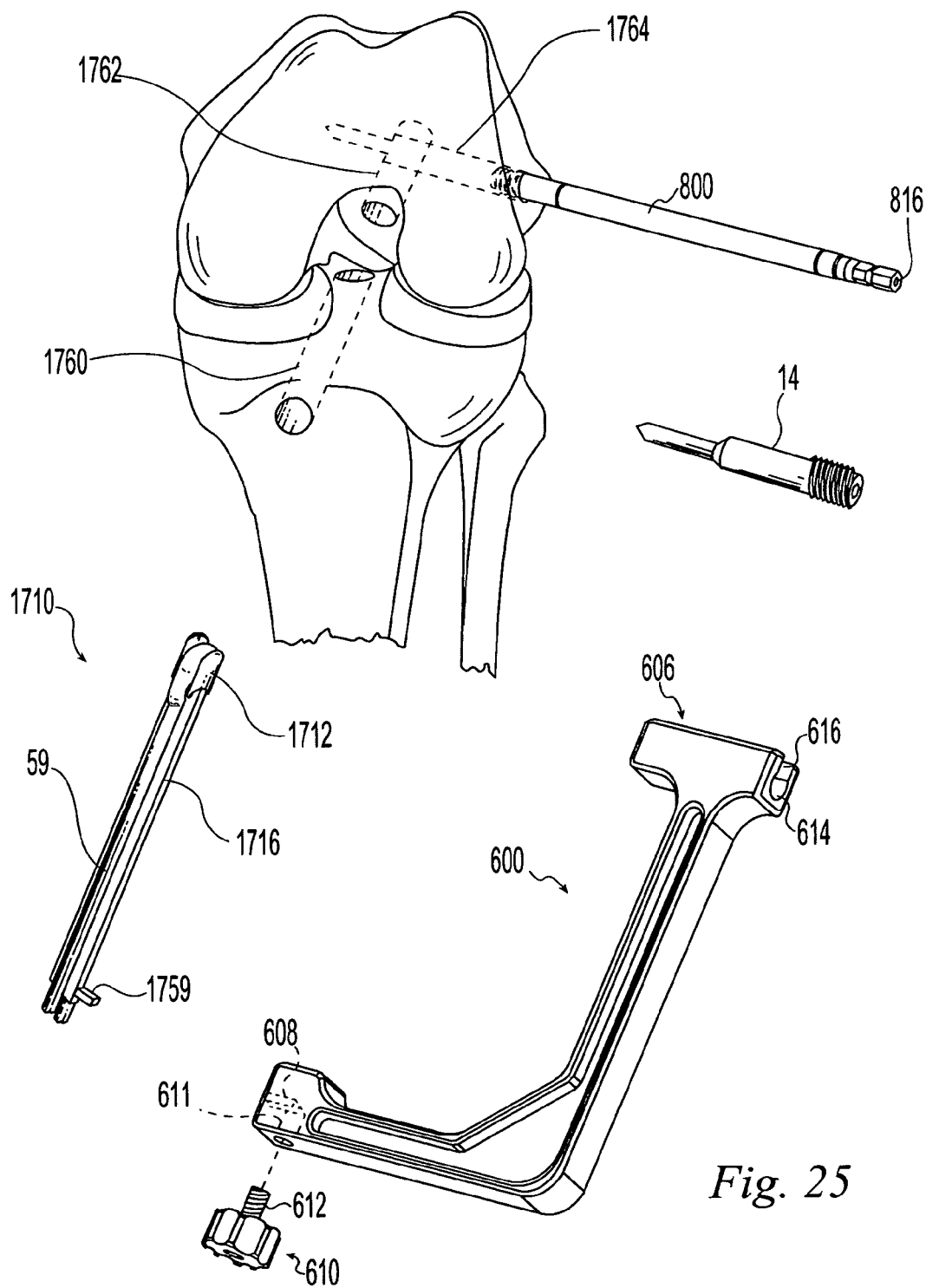
FIG. 25 is a perspective view of a human knee joint showing the insertion of an alternative embodiment of a graft block according to the present invention.

FIGS. 23 and 24 depict an optional attachment mechanism for an intermediate connector such as retaining loop 16. The graft block 12 includes a groove 1600 formed along the distal end 26. The groove 1600 has a smooth convex bottom surface 1602 for supporting the retaining loop 16 and a pair of opposing side walls 1601, 1603 for containing the retaining loop 16. A pair of opposing holes 1604, 1606 are formed through the distal end 26 and open to the bottom surface of the groove 1600 at each end. Each hole 1604, 1606 includes an enlarged counterbore 1608, 1610 for receiving the end of an elongated member 1612 forming the retaining loop 16. The retaining loop 16 is attached to the graft block 12 by threading a first end 1613 of the elongate member 1612 through one of the holes 1604. The first end 1613 may be secured in the hole 1604 by knotting it, inserting a wedge, adhering it, or by other suitable means. In the illustrative embodiment, the first end 1613 is threaded through the hole 1604 so that it extends beyond the counter bore 1608. A first knot 1614 is tied in the first end of the elongate member 1612 and then pulled back so that the first knot 1614 lies within the counter bore 1608. The elongate member is then looped through the channels 50 one or more times to form the desired size of retaining loop 16. The second end of the elongate member 1612 is then threaded through the other hole 1606 through the distal end 26 of the graft block so that the second end extends beyond the counter bore 1610. A second knot is tied in the second end of the elongate member 1612 and then pulled back so that the second knot lies within the counter bore 1610. With the knots contained within the counter bores 1608, 1610, the retaining loop 16 may lie flat against the distal end 26 of the graft block 12 between the opposing walls 1601, 1603.

FIGS. 25-30 depict an alternative embodiment of a graft fixation system 1710 in use to replace the anterior cruciate ligament of a human knee. The fixation system 1710 comprises a graft block 1712, a cross-pin 14, and a pushing member 1716. The graft block 1712 comprises a body 1720 having a proximal end 1724 and a distal end 1726. A "saddle-like" trough 1730 is formed adjacent the distal end 1726 to receive the graft 59. The trough 1730 includes a smooth, convex support surface 1732 formed about an axis 1733 and being bounded at each end by opposing end walls 1734. The end walls 1734 may optionally include through holes for receiving a passing suture like the embodiment of FIG. 1. The end walls 1734 are spaced apart to provide a close fit to the graft 59 as it wraps over the support surface 1732 to contain the graft 59 on the graft block 1712. The support surface 1732 has a sufficiently large radius to support the graft without cutting into the graft 59 or otherwise unduly stressing the graft 59. The outer surface 1728 of the graft block 1712 is cylindrical to fit within the tibial 1760 and femoral 1762 bone tunnels and permit rotation of the graft block within the tunnels 1760, 1762. A semi-circular cutout 1736 is formed adjacent the proximal end 1724 to receive the cross-pin 14. In the illustrative embodiment, the cutout 1736 is formed parallel to the support surface axis 1733 through downwardly projecting extensions 1738 of the end walls 1734 and along the bottom 1740 of the support surface 1732. A pair of sockets 1742 is formed into the bottom 1740 of the support surface 1732 to engage the pushing member 1716. The sockets 1742 are spaced apart axially to position the pushing member between the strands of the graft 59 as they extend proximally away from the graft bock 1712.

The pushing member 1716 includes a flat, plate-like body 1750 having an engagement end 1752 and a grip end 1754. The engagement end includes two prongs 1756 projecting outwardly to engage the sockets 1742 in the graft block 1712. The prongs 1756 may be formed as permanent extensions of the body 1750, or they may be retractable. In the illustrative embodiment of FIG. 30, the prongs 1756 are rods that fit into longitudinal channels 1755 formed in the body 1750. Actuator button 1757 is connected to the prongs 1756 and is movable in a slot 1758 to extend and retract the prongs 1756. An attachment lug 1759 extends from the side of the body 1750 adjacent the grip end 1754 to permit the pushing member 1716 to optionally be connected to the transverse drill guide base 600 for positive positioning of the graft 59/graft block 1712 assembly. With the two prongs 1756 engaged with the sockets 1742, the graft block 1712 may be pressed into the bone tunnels 1760, 1762 and aligned with the transverse hole 1764.

In use, the bone tunnels and transverse hole 1764 are generally prepared as described relative to FIGS. 15 and 16. The tibial tunnel 1760 is drilled to a diameter slightly larger than the graft 59 diameter. The femoral tunnel 1762 is also drilled to a diameter slightly larger than the graft 59 diameter and to a predetermined depth dictated by the desired length of graft to be placed into the femoral tunnel 1762. The transverse hole 1764 is formed to intersect the femoral tunnel 1762. A graft block 1712 is chosen to match the tunnel diameter, and the pushing member 1716 is engaged with the graft block with the prongs 1756 in the sockets 1742. The graft 59 is looped over the support surface 1732 and extended along the sides of the pushing member 1716. The graft 59/graft block 1712 assembly is then passed through the tibial 1760 and femoral 1762 tunnels by applying force to the pushing member 1716. The graft block 1712 is then aligned with the transverse hole 1764.

Insertion and alignment of the graft 59/graft block 1712 assembly may be facilitated by first coupling the pushing member 1710 to the base 600. The attachment lug 1759 is inserted into lug receiving slot 608 of the base 600. Locking bolt 610 is tightened to clamp the lug 1759 in the slot 608. Thus assembled, the semi-circular cutout 1736 in the proximal end 1724 of the graft block 1712 is aligned with the sleeve interface bore 614 both longitudinally and rotationally. The base 600 can now be used as a handle to insert the graft 59/graft block 1712 assembly along the bone tunnels until the cutout 1736 is aligned with the transverse hole 1764. Alignment is confirmed when the locating rod 800 passes through the sleeve interface slot 616 and enters the sleeve interface bore 614.

Once the graft 59/graft block 1712 assembly is seated in the femoral tunnel 1762, the pushing member 1716 is withdrawn. Disengaging the pushing member 1716 from the graft block 1712 may be facilitated by first retracting the prongs 1756 by sliding the actuator button 1757 proximally. The cross pin 14 is then inserted into the transverse hole 1764 and advanced until it engages the semi-circular cutout 1736 and seats in the bone on the medial and lateral sides of the femoral tunnel 1762 as described relative to the previous embodiments.

The combination of the graft block 1712 and the cross pin 14 permits the use of a larger support surface 1732 to reduce stresses on the graft 59 and a smaller cross pin 14 to minimize the size of the transverse hole 1764 and ease insertion as compared to using a pin 14 alone.

In addition to the advantages already stated, the present invention offers other advantages in connecting grafts to bone. One such advantage is that the graft block may be configured to enable the surgeon to pull straight on the end of the graft in order to draw it into the bone tunnel. This pulling direction provides the greatest leverage. The ability to pull straight on the graft in a direction aligned with the graft enables the surgeon to form the bone tunnel with as small a diameter as possible in order to produce a more intimate fit between the graft and the wall of the bone tunnel.

Another advantage of the invention is that the large pin receiving aperture enables the placement of a transverse pin through the graft block in one step and without a guide wire or the need for X-ray visualization.

Another advantage of the invention is that it permits delicate handling of the graft and its secure attachment to the graft block outside of the body where it can be visualized and handled with ease. The blind attachment of the graft block/graft assembly within the bone tunnel involves connecting two easily manipulated, robust, positively engaging pieces with little chance for damage to the graft or a partial attachment.

It will be understood by those skilled in the art that numerous improvements and modifications may be made to the preferred embodiment of the invention disclosed herein without departing from the spirit and scope thereof.

What is claimed is:

1. A graft retaining system for retaining a graft in a bone tunnel comprising:
   a graft block having a proximal end and a distal end, the graft block being sized to slidingly fit within the bone tunnel, the graft block including a distally-facing support surface at the distal end for supporting an intermediate connector, a pair of transverse throughbores being formed through the support surface;
   an intermediate connector connecting a predetermined portion of the graft and a predetermined portion of the graft block, the intermediate connector formed of an elongated member forming a loop supported by the support surface of the graft block, the elongated member having a first end and a second end, at least one of the first and second ends being threaded in one direction through at least one of said transverse throughbores;
   means for preventing said threaded end from passing back through said at least one transverse throughbore; and
   means on said graft block for receiving a separate transverse member to attach the graft block at a predetermined point along the length of the tunnel, the transverse member being situated transverse to the axis of the bone tunnel and through the loop created by said intermediate connector, said support surface comprising a convex surface bounded on at least two sides by projecting side walls to retain the intermediate connector on the convex surface, wherein said intermediate connector is a suture-like material and wherein said pair of transverse throughbores are formed through the support surface generally parallel to the side-walls from a first portion of the convex surface to a second portion of the convex surface, each of the throughbores being countersunk at at least one end such that the ends of the intermediate connector may be secured to the graft block by being threaded through respective throughbores knotted and pulled back into the countersunk ends of the throughbores.

* * * * *